United States Patent
McDonald et al.

(10) Patent No.: US 11,865,335 B2
(45) Date of Patent: Jan. 9, 2024

(54) DEVICES, SYSTEMS, METHODS AND ASSEMBLIES FOR MEDICAL ELECTRODES

(71) Applicant: Baymatob Pty Ltd, Sydney (AU)

(72) Inventors: Sarah Catherine McDonald, Sydney (AU); Rishi Ramakrishnan, Sydney (AU)

(73) Assignee: Baymatob Pty Ltd, Sydney (AU)

( * ) Notice: Subject to any disclaimer, the term of this patent is extended or adjusted under 35 U.S.C. 154(b) by 105 days.

(21) Appl. No.: 17/424,129

(22) PCT Filed: Jan. 24, 2020

(86) PCT No.: PCT/AU2020/050045
§ 371 (c)(1),
(2) Date: Jul. 19, 2021

(87) PCT Pub. No.: WO2020/150784
PCT Pub. Date: Jul. 30, 2020

(65) Prior Publication Data
US 2022/0096825 A1    Mar. 31, 2022

(30) Foreign Application Priority Data

Jan. 25, 2019 (AU) ............................ 2019900236
Jan. 25, 2019 (AU) ............................ 2019900237

(51) Int. Cl.
| | |
|---|---|
| *A61N 1/08* | (2006.01) |
| *A61B 5/25* | (2021.01) |
| *G06K 7/10* | (2006.01) |
| *G06K 19/07* | (2006.01) |
| *A61B 5/24* | (2021.01) |

(52) U.S. Cl.
CPC .............. *A61N 1/08* (2013.01); *A61B 5/24* (2021.01); *A61B 5/25* (2021.01); *G06K 7/10297* (2013.01); *G06K 19/0723* (2013.01); *A61B 2562/08* (2013.01)

(58) Field of Classification Search
CPC ........ A61N 1/08; A61B 5/25; G06K 7/10297; G06K 19/0723
USPC ....................................................... 235/451
See application file for complete search history.

(56) References Cited

U.S. PATENT DOCUMENTS

| | | | |
|---|---|---|---|
| 9,037,477 B2 | 5/2015 | Bardy et al. | |
| 9,427,590 B2 | 8/2016 | Doerr | |
| 2006/0226985 A1 | 10/2006 | Goodnow et al. | |
| 2007/0046471 A1* | 3/2007 | Nyalamadugu | G06K 7/10079 |
| | | | 340/572.1 |

(Continued)

FOREIGN PATENT DOCUMENTS

| | | |
|---|---|---|
| WO | 2016145314 A1 | 9/2016 |
| WO | 2018102874 A1 | 6/2018 |

OTHER PUBLICATIONS

PCT/AU2020/050045, "International Search Report and Written Opinion", dated Mar. 11, 2020, 15 pages.

(Continued)

*Primary Examiner* — Ahshik Kim
(74) *Attorney, Agent, or Firm* — Kilpatrick Townsend & Stockton LLP

(57) ABSTRACT

A device including at least one medical electrode; a radio-frequency (RF) tag with an identifier (ID) that identifies the at least one medical electrode; and at least one substrate that attaches the at least one medical electrode to the RF tag.

19 Claims, 13 Drawing Sheets

(56) References Cited

U.S. PATENT DOCUMENTS

| | | | |
|---|---|---|---|
| 2007/0052603 A1* | 3/2007 | Nyalamadugu | H01Q 7/00 |
| | | | 343/742 |
| 2011/0166491 A1 | 7/2011 | Sankai | |
| 2014/0066741 A1 | 3/2014 | Peterson et al. | |
| 2015/0199487 A1* | 7/2015 | Grauds | A61L 2/10 |
| | | | 250/365 |
| 2015/0317896 A1* | 11/2015 | Planton | G08B 21/182 |
| | | | 340/584 |
| 2016/0338798 A1 | 11/2016 | Vora et al. | |
| 2016/0371516 A1* | 12/2016 | Debates | G06K 19/07345 |
| 2021/0015407 A1* | 1/2021 | Bohm | A61B 5/685 |

OTHER PUBLICATIONS

PCT/AU2020/050045, "International Preliminary Report on Patentability", dated Aug. 5, 2021, 10 pages.

* cited by examiner

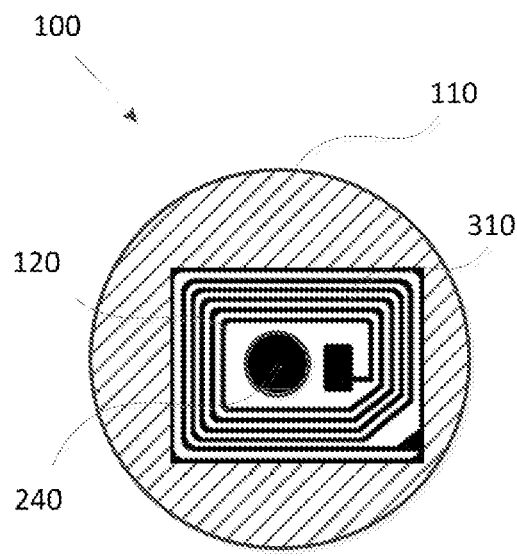
(A)
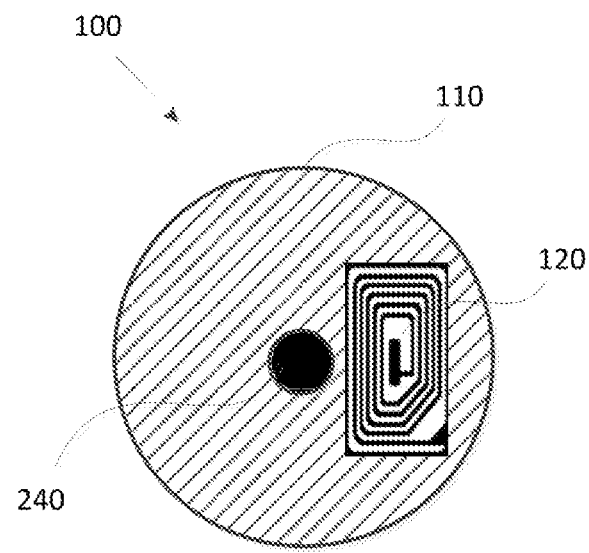
(C)
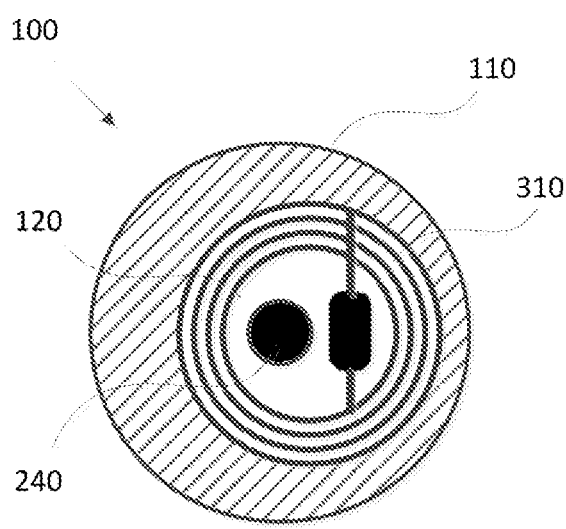
(B)
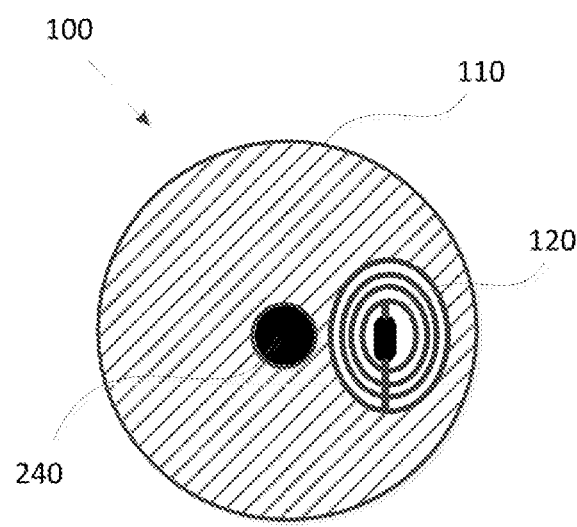
(D)
Figure 6

DEVICES, SYSTEMS, METHODS AND ASSEMBLIES FOR MEDICAL ELECTRODES

RELATED APPLICATIONS

This application is a U.S. National Phase of International Application No. PCT/AU2020/050045, filed Jan. 24, 2020, claiming priority to Australian Provisional Patent Application No. 2019900236, filed Jan. 25, 2019, and Australian Provisional Patent Application No. 2019900237, filed Jan. 25, 2019, contents of which are hereby incorporated by reference in their entirety.

TECHNICAL FIELD

The present disclosure relates to medical electrodes, and to devices, systems methods and assemblies for monitoring and/or controlling the use of medical electrodes.

BACKGROUND

Medical electrodes have been used in monitoring or delivering electrical signals from or to a human or animal body. Typically, a medical electrode includes a conductive member that can be placed on and electrically connected to the skin of a patient, the conductive member being also connected to an external medical device that monitors or outputs electrical signals.

Various types of medical electrodes have been developed. For example, FIGS. 12(A) and 12(B) illustrate the front side and back side views of different medical electrodes, each of which includes the following components:
  a) a connector 1210 for joining the electrode to a medical device, the connector 1210 being made of conductive material, e.g., metal;
  b) one or more flexible sheets or films 1220 for supporting the connector 1210, which may be made of e.g., cloth, plastic, foam, or any other suitable material for mechanically supporting the connector 1210 on the patient's body;
  c) a conductive area 1230, e.g., conductive gel, for electrically connecting the connector 1210 to the skin of the patient; and
  d) adhesive 1240 for securing the flexible sheet or film 1220 on the patient's body.

However, the arrangement of these components in different medical electrodes may vary, and for each component its shape, dimensions and material used may be different. As a result, different types of medical electrodes may provide different signal quality and deliver different performance.

For example, different types of medical electrodes may present different signal-to-noise ratios, different duration of attachment, and/or different shelf life. Further, some medical electrodes may be designed for a specific type of medical device, and using these electrodes with other medical devices may result in poor signal quality or even cause damage to the electrodes or the medical devices.

Although some medical institutions (e.g., government institutions, hospitals or clinics) have set out regulatory standards or policies regarding the use of medical electrodes, in reality these standards or policies may be difficult to enforce and their effects are hard to test. Further, in some cases two different electrode types may both comply with required standards or regulations, but still present variations in their results due to each using different:

a) connector material or conductive gel which could directly impact signal quality, noise and artefacts caused by patient movement;
  b) area of conductive surface which could vary incoming signals and the risk of unwanted crosstalk caused by other muscles or bodily functions; or
  c) non-conductive adhesive areas and electrode material which could impact how long and under what conditions an electrode is best used.

Some electrode manufacturers have been providing documentation and labelling on packages of electrodes to inform the user about the intended uses or applications of the electrodes. For example, some electrode manufacturers colour code electrodes to provide indication of suitability for a given application. However, to a standard clinical user, these methods do not provide a clear indication of the potential impacts on electrical signals from using these electrodes with a particular medical device.

Currently, technologies for monitoring the use of different types of electrodes, and identifying whether the electrodes used are in fact compatible with the medical device, are insufficiently effective at least in some applications.

In addition, medical device and electrode manufacturers often have limited ability to track the specific device-and-electrode combinations being used, or to control the use of the electrodes outside their recommended uses. This presents further issues in performance monitoring and quality control of electrode products and the implementation of suitable product improvements.

It is desired to address or ameliorate one or more disadvantages or limitations associated with the prior art, or to at least provide a useful alternative.

SUMMARY

In a first aspect, there is provided a device including: at least one medical electrode; a radio-frequency (RF) tag with an identifier (ID) that identifies the at least one medical electrode; and at least one substrate that attaches the at least one medical electrode to the RF tag.

In a non-limiting embodiment, the at least one substrate is a removable substrate that is arranged to be manually removable from the medical electrode and the RF tag.

In another embodiment, the at least one substrate includes: a first substrate layer removably attached to one side of the medical electrode and one side of the RF tag; and a second substrate layer removably attached to an opposite side of the medical electrode and opposite side of the RF tag.

In yet another non-limiting embodiment, the at least one substrate is an integral substrate that is arranged to maintain the at least one medical electrode together with the RF tag in use.

In an embodiment, the device includes a plurality of medical electrodes and a shared substrate that holds the plurality of medical electrodes and the RF tag together.

In an example, the RF tag is attached upon the electrode member and positioned next to an electrode connecter of the electrode member.

In yet another example, the RF tag includes an antenna around an electrode connector of the medical electrode.

In a second aspect, there is provided a device including: at least one conductive cable for a medical device that monitors or generates electrical signals; a conductive connector at one end of the conductive cable for connecting to a medical electrode; and a radio-frequency (RF) reader directly connected to the same end of the conductive cable for reading an RF tag attached to the medical electrode.

In a non-liming example, the at least one conductive cable includes: a signal line to carry signals to and/or from the medical device; and a power line to power the RF reader and/or to carry signals to and/or from the RF reader.

In a third aspect, there is provided a system including: a radio-frequency (RF) reader that reads an RF tag attached to a medical electrode to determine a tag identifier (ID) that identifies the medical electrode; and a medical device that operates with the medical electrode having a device identifier (ID) that identifies the medical device.

In a non-limiting embodiment, the medical device, a server or a terminal computing device including a data storage device that stores data representing the tag ID linked to the device ID.

In another embodiment, the data storage device stores data representing the tag ID and the device ID linked to signals recorded by the medical device using the medical electrode.

In yet another non-limiting embodiment, use of the medical electrode with the medical device is controlled based on a control signal determined from a combination of the tag ID and the device ID.

In an example, the third aspect includes a control system that: receives the tag ID and the device ID; accesses data representing pre-determined compatibilities between a plurality of stored device IDs and stored tag IDs stored in a data storage device; and generates the control signal by determining whether the tag ID and the device ID are compatible according to the pre-determined compatibilities.

In a fourth aspect, there is provided a method comprising the steps of: reading an RF tag attached to a medical electrode to determine a tag identifier (ID) that identifies the medical electrode; accessing a device identifier (ID) that identifies a medical device that operates with the medical electrode; and controlling use of the medical electrode with the medical device based on a control signal determined from a combination of the tag ID and the device ID.

In an example, the method includes the step of storing data representing the tag ID linked to the device ID.

In another example, the method includes the step of storing data representing the tag ID and the device ID linked to signals recorded by the medical device using the medical electrode.

In yet another example, the method further includes the steps of: receiving the tag ID and the device ID; accessing data representing pre-determined compatibilities between a plurality of stored device IDs and stored tag IDs stored in a data storage device; and generating the control signal by determining whether the tag ID and the device ID are compatible according to the pre-determined compatibilities.

In a fifth aspect, there is provided, a computer-implemented method, including the steps of: receiving, via a radio-frequency (RF) reader, tag identification data representing a tag identifier (ID) from an RF tag attached to a medical electrode; accessing device identification data representing a device identifier (ID) associated with a medical device operable to use at least one medical electrode; determining a control signal corresponding to the combination of the tag ID and the device ID; and controlling the use of the medical electrode with the medical device based on the control signal.

In an example, the control signal is determined by sending the combination of the tag ID and the device ID to an external device; and receiving the control signal from the external device.

In yet another non-limiting example, controlling the use of the medical electrode with the medical device further includes: outputting an alert if the use of the medical electrode is prohibited or limited.

In a sixth aspect, there is provided, a computer-implemented method, including the steps of: receiving, from a medical device operable to use at least one medical electrode, tag identification data representing a tag identifier (ID), the tag identification data being obtained from an RF tag attached to the medical electrode; obtaining device identification data representing a device identifier (ID) associated with the medical device; determining a control signal corresponding to the combination of the tag ID and the device ID; and outputting the control signal that controls the use of the medical electrode with the medical device.

In an example, outputting the control signal includes: sending the control signal to the medical device.

In a seventh aspect, there is provided a device including: a plurality of medical electrodes; a corresponding plurality of radio-frequency (RF) tag, each having an identifier (ID) that identifies a corresponding one of the plurality of medical electrodes; and at least one substrate removably attached to the plurality of medical electrodes and the plurality of RF tags.

In an eighth aspect, there is provided an assembly including: a medical device that monitors or generates electrical signals; a conductive connector in or on the medical device for connecting to a medical electrode; and a radio-frequency (RF) reader in or on the medical device for reading an RF tag attached to the medical electrode.

BRIEF DESCRIPTION OF THE DRAWINGS

Some embodiments of the present invention are hereinafter described, by way of example only, with reference to the accompanying drawings, wherein:

FIGS. 6(A) to 6(D) show some other examples of the trackable electrode device;

DETAILED DESCRIPTION

Figure 1B:
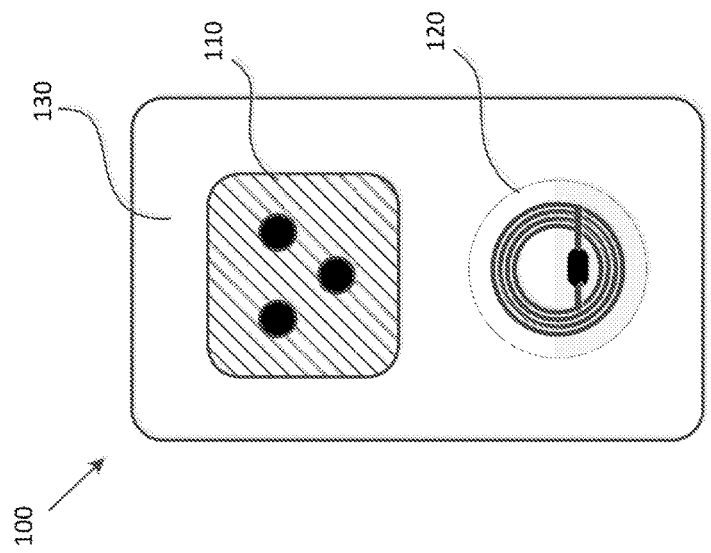
FIGS. 1(A) and 1(B) illustrate examples of a trackable electrode device.

Provided herein are systems and methods for monitoring the use of medical electrodes. The provided systems and methods allow identification of whether an electrode is in fact compatible with a specific medical device. The results can be used to control the use of the electrode with that medical device. Accordingly, the use of electrodes outside their recommended uses can be prevented or reduced.

According to at least some embodiments, the provided systems and methods further enable tracking of the use of electrodes with medical devices, and tracking of the performances of the electrodes when used with different medical devices. Accordingly, the compatibility of different electrodes with different medical devices can be further assessed and analysed over time, so that future use of the electrodes may be optimised or improved based on their previous performances.

According to at least some embodiments, the provided systems and methods further allow monitoring of abnormalities that occurred during the use of the medical electrodes. The monitoring results and the abnormalities detected can be subsequently reported to the manufacturer of the electrodes. This provides a more effective and efficient way of performance monitoring and quality control for electrode products, and allows product improvements to be implemented in a timely manner.

It is noted that in the Figures, like reference numerals are used to identify like parts throughout the Figures. Referring now to FIG. 1(A), there is provided an example of a trackable electrode device 100. The trackable electrode device 100 includes at least one electrode member 110 (which may also be referred to as a "medical electrode" or "traditional electrode") and a radio-frequency (RF) tag 120. The electrode member 110 and the RF tag 120 are attached or fitted in proximity to each other within or upon a substrate 130. The substrate 130 attaches the electrode member 110 to the RF tag 120, i.e., holds the electrode member 110 and the RF tag 120 together.

The substrate 130 can be made from one or more flexible materials, e.g., cloth, paper, plastic or foam. The substrate 130 may be separable from the electrode member 110 and the RF tag 120, i.e., the substrate 130 may be removed from the electrode member 110 and the RF tag 120 during use by a person. Thus, the substrate 130 may be in the form of a removable sheet or cover that is removed by a clinician or operator before or after applying the electrode member 110 to the patient or connecting it to the medical device. This form of the substrate 130 may be referred to as a "removable substrate", which is discussed in further detail below. During storage and initial manual handling, this removable substrate holds the electrode member 110 and the RF tag 120 in a preselected arrangement; then the removable substrate is removed from the electrode member 110 and/or the RF tag 120 for application to (and generally adhesion to) the subject's skin or the external medical device. The RF tag 120 may have its own adhesive/backing independent of the electrode member 110, so once the removable substrate is removed, the electrode member 110 and/or the RF tag 120 are no longer attached to and held by the substrate 130.

Alternatively, the substrate 130 may remain integral with the electrode member 110 and the RF tag 120 during use, i.e., the substrate 130 is not removed from the electrode member 110 and the RF tag 120 during use. Thus the substrate 130 may be in the form of a flexible pad or sheet integrated with the electrode member 110. This form of the substrate 130 may be referred to as an "integral substrate". This is described in further detail below.

In some embodiments, the trackable electrode device 100 further includes a non-electrode adhesive pad for facilitating securing the medical device to the patient's body, and/or to the medical electrodes members. The RF tag 120 may be embedded or accommodated in the non-electrode adhesive pad. The non-electrode adhesive pad may be located at or proximate to the centre of the trackable electrode device 100, or any other location on the trackable electrode device 100 that allows the RF tag 120 to communicate with an external RF reading device. In a further embodiment, the electrode member 110 may have the same structure as a known medical electrode device.

Figure 2:
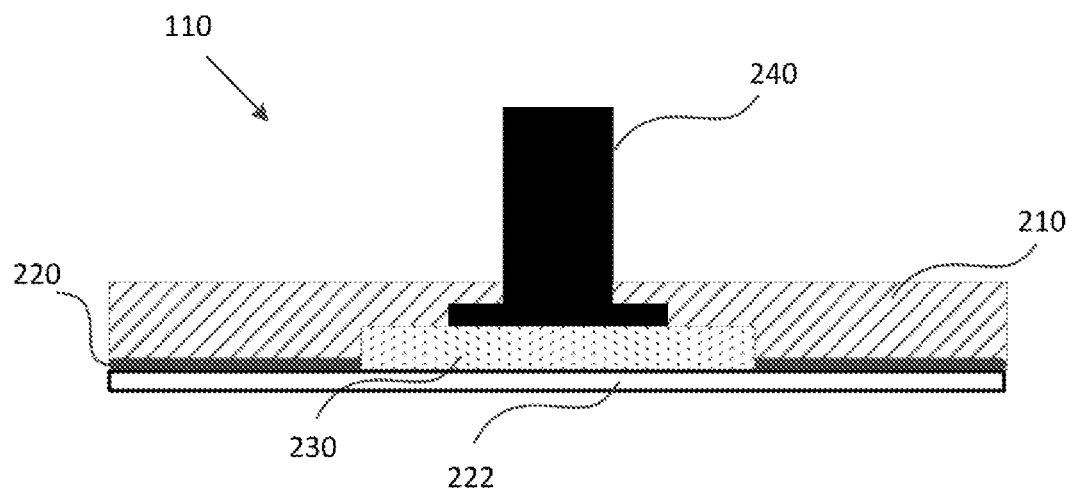
FIG. 2 shows an example of an electrode member of the trackable electrode device.

Referring now to FIG. 2, there is provided an example of the electrode member 110. In this example, the electrode member 110 includes a flexible sheet 210 that is adaptable to the contour of the skin of a patient. The flexible sheet 210 is made of an insulating material, e.g., cloth, plastic, closed cell foam, or any other suitable insulating material.

The electrode member 110 further includes an adhesive layer 220 containing a sticking substance on one side of the flexible sheet 210, for securing the flexible sheet 210 to the skin of the patient. The sticking substance is referred to as an adhesive, which may include but not be limited to acrylic, silicone, and polyurethane based adhesives. The electrode member 110 further includes a removable cover 222, which may form the (removable) substrate 130, that covers the adhesive layer 220 during storage, and which is removed by a clinician shortly before applying the adhesive layer 220 to the skin of the patient.

Also provided on that side of the flexible sheet 210 is a conductive area 230. The conductive area 230 is formed of conductive substance that can electrically connect the skin of the patient with an electrode connector 240 (also referred to as an "electrode-side connector" herein), the conductive substance being, e.g., conductive hydrophilic gel. The electrode-side connector 240 is made of a conductive material (e.g., metal), and may be a fastener, and in some embodiments has a shape similar to a male/female snap fastener, or has the form of a tab, wire or custom connector, and can be electrically connected, via a flexible conductive cable (also known as a "lead") or directly, to an external medical device that monitors or generates electrical signals. While FIG. 2 illustrates one example of the electrode member 110, the electrode member 110 may alternatively have any other suitable structure and components known to a person skilled in the art.

Figure 3:
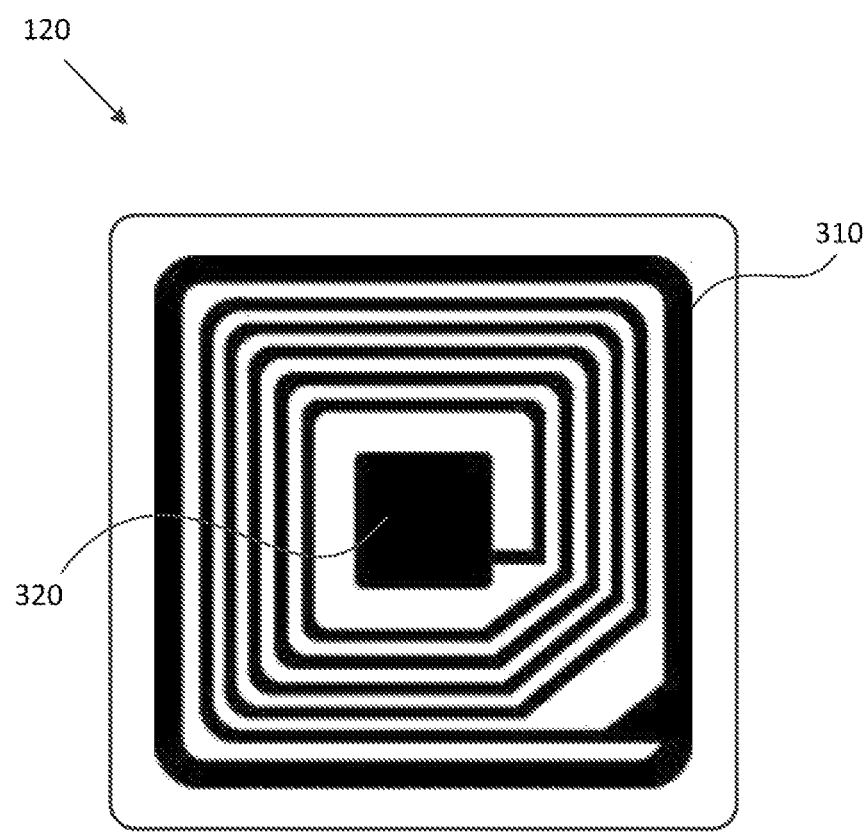
FIG. 3 illustrates an example of an RF tag of the trackable electrode device.

Referring now to FIG. 3, there is provided an example structure of the RF tag 120, which includes an antenna 310 and an integrated circuit 320. The RF tag 120 may include, e.g., a radio-frequency identification (RFID) tag or a near-field communication (NFC) tag, which can be read by an RFID reader or an NFC reader of an external electronic device. Alternatively, the RF tag 120 may be any other suitable type of compact RF communication device. Although not shown in FIG. 3, the RF tag 120 can further include a tag connector that connects to a cooperating tag holder of the medical device 200, e.g., cooperating press-stud parts and/or an adhesive.

The RF tag 120 stores, e.g., in the integrated circuit 320, tag identification data representing a tag identifier (ID) associated with the electrode member 110. The tag ID can be used by an external device for determining detail information of the trackable electrode device 100, and in particular, detail information of the electrode member 110, including for example, any one or more of the following:
a) the type of the electrode member 110;
b) the components and composition (e.g., number and position of the electrode-side connectors, dimensions and materials of the flexible sheet, the adhesive layer, the conductive area, and a type of the electrode-side connector) of the electrode member 110;
c) the manufacturer of the electrode member 110;
d) the manufacture date of the electrode member 110;
e) a batch number of the electrode member 110;
f) an expiry date or shelf life of the electrode member 110; and
g) a maximum or recommended attachment duration of the electrode member 110.

For example, an exemplary tag ID is in the form of an alphanumeric sequence "ABCDEDZX", where A represents the connector type, B represents the flexible sheet type, C represents the application(s) for which the trackable electrode will be used, G represents the conductive gel type, E represents the adhesive type, D represents the date of manufacture, Z represents the batch number or batch identifier (batch ID), and X represents the product identifier within a batch.

Optionally, the tag identification data may include additional information regarding the trackable electrode device 100 and/or the electrode member 110, e.g., a product serial number of the trackable electrode device 100 or the electrode member 110. The tag identification data may also include any other suitable information.

The detail information of the electrode member 110 may be used for determining how the trackable electrode device 100 should be used, and/or whether it should be used with a certain monitoring or stimulating medical device. That is, the compatibility between the trackable electrode device 100 and an external medical device can be determined using the tag ID.

Accordingly, an external medical device can control the use of the trackable electrode device 100 based on the determined compatibility. For example, controlling the use by allowing the use of a compatible trackable electrode device 100, or by prohibiting the use of an incompatible trackable electrode device 100. In some embodiments, the trackable electrode device 100 may be partly compatible with a medical device, i.e., the electrode member 110 may be suitable for some functions of the medical device, but unsuitable for other functions of the medical device. Accordingly, the medical device may allow the trackable electrode device 100 to be used for those suitable functions, while prohibiting other functions.

In some embodiments, the external medical device may notify a user that the trackable electrode device 100 the user is attempting to use is not compatible or not fully compatible with the medical device, e.g., by triggering an alarm or displaying a warning message on a display of the medical device.

Referring again to FIG. 1(A), the substrate 130 fits and holds the RF tag 120 in proximity to the electrode member 110. The substrate 130 is made of a flexible material, e.g., cloth, paper, plastic or foam, so that when the electrode member 110 is attached to the skin of a patient, the substrate 130 can flex in a similar manner as the flexible sheet 210 of the electrode member 110. This facilitates securing the trackable electrode device 100 to the patient's body or to the medical device.

Figure 4:
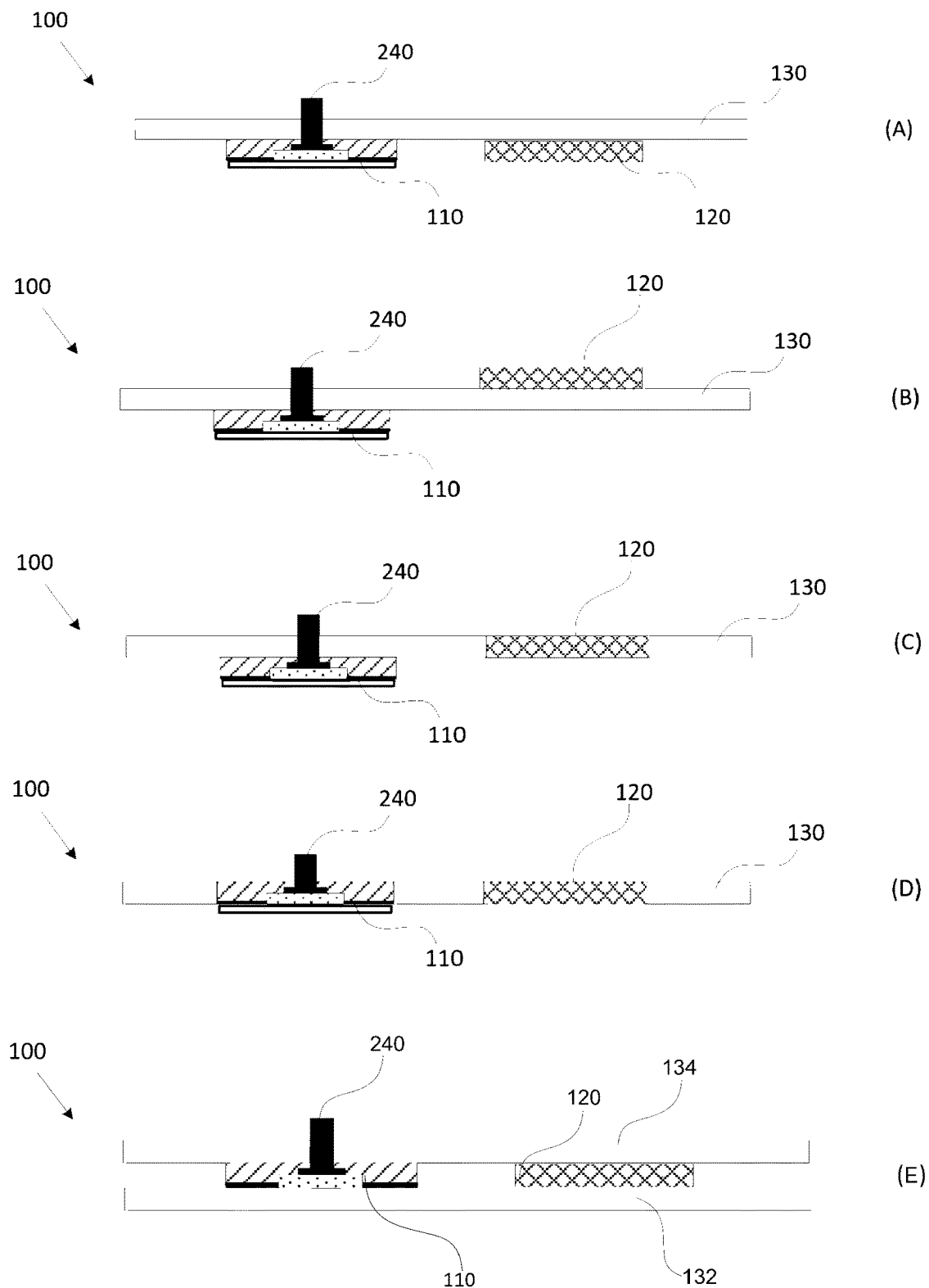
FIGS. 4(A) to 4(E) show cross-sectional views of some examples of the trackable electrode device of FIG. 1(A) along line x'-x'.

FIGS. 4(A) to 4(D) illustrate some possible arrangements of the electrode member 110 and the RF tag 120 fitted within or upon the substrate 130. As shown in FIG. 4(A) and FIG. 4(B), the electrode member 110 may be attached to one side of the substrate 130, with the electrode member 110 passing through the substrate 130 so that an end of the electrode-side connector 240 is exposed on the other side of the substrate 130. The RF tag 120 may be attached to either side of the substrate 130. In an embodiment FIGS. 4(A) and 4(B) the substrate 130 may be integral to the electrode member 110. That is, where the at least one substrate is an integral substrate, the substrate is arranged to maintain the at least one medical electrode together with the RF tag in use, as it is not removed when the electrode member 110 is attached to the patient and/or medical device. In an embodiment, the flexible sheet 210 may form at least a portion of the integral substrate 130.

For example, when the substrate 130 is integral to the electrode member 110, the flexible sheet 210 of the electrode member 110 is permanently bonded to the substrate 130, by way of adhesives or other suitable engagement means. Further, the RF tag 120 and the electrode member 110 may be also permanently bonded to the substrate 130, by way of adhesives or other suitable engagement means.

In another example shown in FIG. 4(C), the substrate 130 is integral to the electrode member 110. In this example, the electrode member 110 is attached to the substrate 130 in the same way as in FIG. 4(A) and FIG. 4(B), whilst, the RF tag 120 is integrally formed with the substrate 130, for example by embedding the RF tag 120 within the (integral) substrate 130 or including it when manufacturing the (integral) substrate 130.

Alternatively, another example is provided as shown in FIG. 4(D), where the substrate 130 is integral to the electrode member 110. In this example, both the electrode member 110 and the RF tag 120 may be embedded within the (integral) substrate 130. For example by embedding the RF tag 120 within the (integral) substrate 130 or including it when manufacturing the (integral) substrate 130.

Alternatively, FIG. 4(E) illustrates a possible arrangement of the electrode member 110 and the RF tag 120, wherein the substrate includes:
a) a first substrate layer 132 (e.g., a film or liner) removably attached to one side of the medical electrode 110 and one side of the RF tag 120; and
b) a second substrate layer 134 (e.g., a film or liner) integrally attached to an opposite side of the medical electrode 110 and opposite side of the RF tag 120.

In this embodiment, the first substrate layer 132 may be removable and the second substrate 134 may be integral. The first substrate layer 132 function in a similar way to the removable cover 222, in that it is removable to expose an adhesive surface but does not include any adhesive surfaces. In this example, the first substrate layer 132 is removed to expose the adhesive layer 220 on the patient-side of the medical electrode 110 mentioned previously. Further, the first substrate layer 132 may also be removed to expose an RF tag adhesive layer (not shown) similar to that of the adhesive layer 220 that is provided to the patient-side surface of the RF tag. The adhesive layer 220 on the patient-side of the medical electrode 110 and/or said RF tag adhesive layer are arranged to aid adhering the trackable electrode device 100 to the patient.

In any of the above embodiments where the substrate 130 is integrally formed with the electrode member 110, a patient adhesive layer (not shown) may be provided on the patient-side of the substrate 130 (i.e. the side of the substrate 130 facing the skin of the patient), which may further facilitate securing the trackable electrode device 100 on the body of the patient. In a further optional embodiment, a medical device adhesive layer may be provided to the device-side of the second substrate layer 134, i.e., the side facing the medical device 200, to aid in attaching the medical electrode 110 to the medical device for any integral substrate 130 herein described.

In alternate embodiments, the substrate 130 may be manually removable from the at least one electrode member 110 and the RF tag 120. For example, FIG. 4(A) may show an alternate embodiment where the flexible sheet 210 of the electrode member 110 is non-permanently bonded to the substrate 130, by way of adhesive provided to the device-side of the flexible sheet 210 that permits separation, or other suitable engagement means. Further, the RF tag 120 and the electrode member 110 may be also be non-permanently bonded to the substrate 130, by way of adhesives that permit separation, or other suitable engagement means.

Removal of the removable substrate 130 may occur to enable the electrode member 110 to be fastened to a medical device 200 using the aforementioned adhesive provided to the device-side of the flexible sheet 210. In such an embodiment, a second substrate layer 132 may form the removable cover 222, or the shared removable cover if there is a plurality of electrode members 110. In this example, the removable cover 222 is removed to expose the adhesive layer 220 mentioned previously. Further, an additional removable cover (not shown) may also be provided to the patient-side of the electrode member 110, that when removed exposes an additional adhesive layer (not shown) provided to the patient-side surface of the RF tag 120.

In this example, the RF tag 120 may be fastened to the medical device 200 when the electrode member(s) 110 are fastened thereto, e.g., by a fastener of the medical device 200 (e.g., in the leads or a fastener on the housing of the medical device 200), which may include the OLI™ device to which a plurality of electrode members 110 can be fastened, as described in Australian Provisional Patent Application No. 2016905046 titled "Apparatus for monitoring pregnancy or labour" and/or in PCT Application No. PCT/AU2017/051346 of the same name.

Alternatively, an alternate embodiment is also provided by FIG. 4(E), wherein the electrode member 110 and the RF tag 120 are non-permanently attached to two removable substrates, which may include:
  a) a first substrate layer 132 (e.g., a film or liner) removably attached to one side of the medical electrode 130 and one side of the RF tag 120; and
  b) a second substrate layer 134 (e.g., a film or liner) removably attached to an opposite side of the medical electrode 130 and opposite side of the RF tag 120.

In use, a user may peel off the first substrate layer 132 to expose the adhesive beneath that is provided to the patient-side of the electrode member 110 and the RF tag 120, and apply the remaining assembly of the second substrate layer 134, electrode member 110 and the RF tag 120 on the patient's skin. The assembly will adhere to the patient's skin because of the exposed adhesive, which was previously covered by the first substrate layer 132. In this regard, the first substrate layer 132 functions similarly to the removable cover 222. However, the first substrate layer 132 simultaneously covers adhesive provided to both the patient-side of the electrode member 110 and the RF tag 120.

Once the electrode 130 and the RF tag 120 are secured to the patient's skin, the user may then peel off the second substrate layer 134 to expose the adhesive beneath. The user can then attach the medical device 200 to the exposed adhesive surface of the electrode member 110 (and optionally the RF tag 120), thereby securing the medical electrode 110 (and optionally the RF tag 120) to the medical device 200. After the monitoring is completed, the used electrode member 110 and the RF tag 120 may be removed from the medical device 200 and from the patient's skin, and disposed of.

As described hereinbefore, the electrode member 110 and the RF tag 120 may take any suitable form different from those shown in FIG. 1(A). For example, FIG. 1(B) illustrates another example of the trackable electrode device 100 that includes a different type of electrode member 110 and a different type of RF tag 120.

Figure 1A:
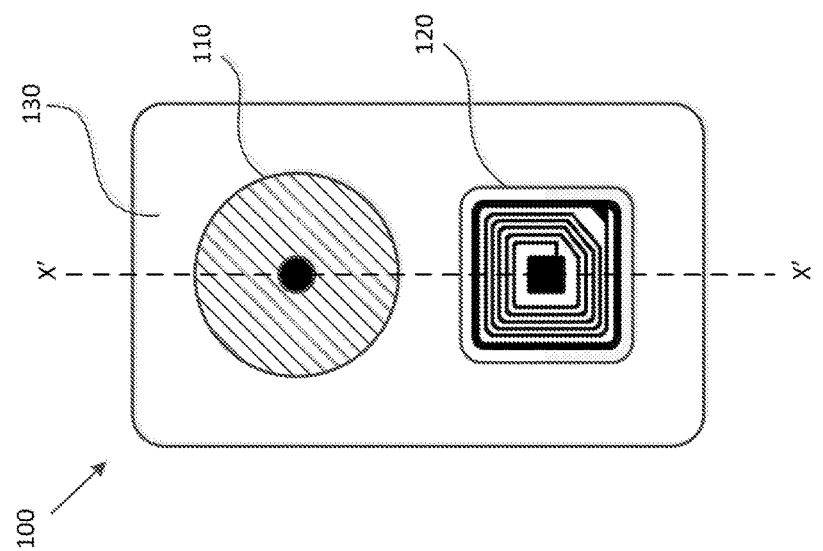

Further, although the trackable electrode device 100 shown in FIG. 1(A) and FIG. 1(B) includes a single electrode member 110, the trackable electrode device 100 may alternatively include a plurality of electrode members 110. The trackable electrode device 100 can include a shared flexible sheet connected to a plurality of conductive areas 230 (one for each of the plurality of electrode members 110), and the trackable electrode device 100 can include a shared removable cover that covers a plurality of the adhesive layers 220 (one for each of the plurality of electrode members 110). The RF tag 120 can include one tag ID that represents the trackable electrode device 100 (which include its plurality of electrode members 110), or the RF tag 120 can include a plurality of tags IDs for the respective electrode members 110 of the trackable electrode 100.

Figure 5A:
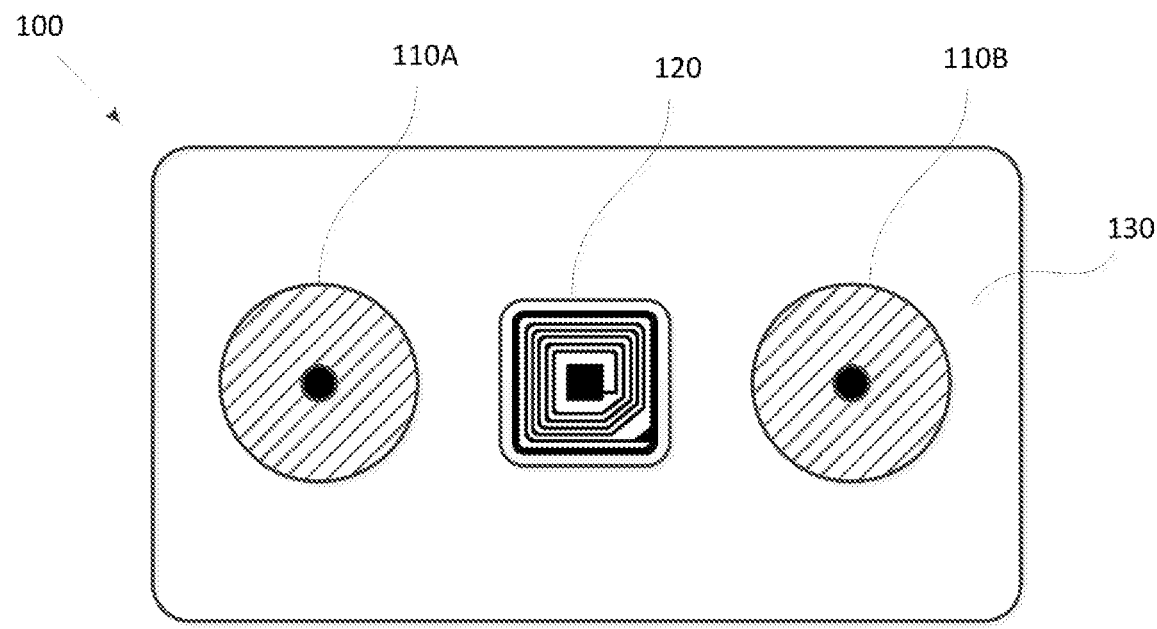
FIG. 5(A) shows another example of the trackable electrode device.

FIG. 5(A) shows another example of the trackable electrode device 100, which includes two electrode members 110A, 110B and a single RF tag 120. The two electrode members 110A, 110B may have the same structure and composition. Alternatively, the structure and composition of the two electrode members 110A, 110B may be different from each other. An external device may use the tag identification data stored in the RF tag 120 to determine detailed information relating to each of the two electrode members 110A and 110B.

Figure 5B:
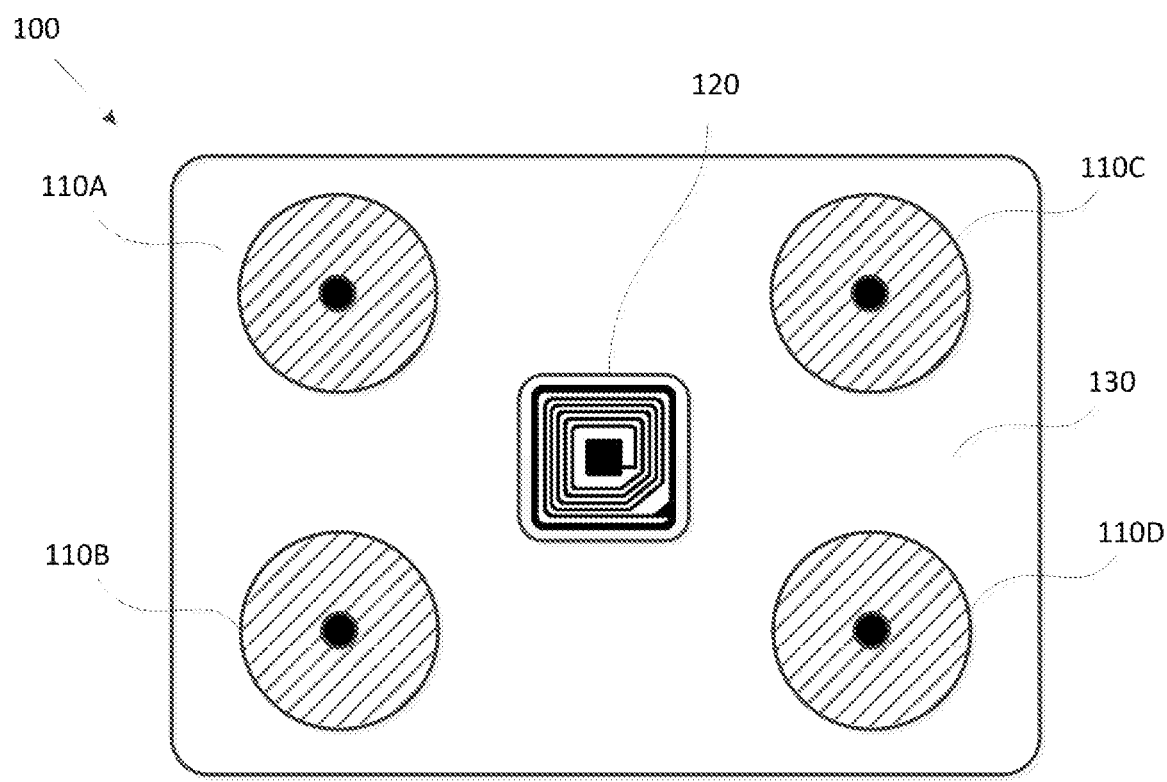
FIG. 5(B) shows a further example of the trackable electrode device.

FIG. 5(B) shows another example of the trackable electrode device 100, which includes four electrode members 110A, 110B, 110C and 110D, as well as a single RF tag 120. An external device may use the tag identification data stored in the RF tag 120 to determine detailed information relating to each of the four electrode members 110A, 110B, 110C and 110D.

Figure 13:
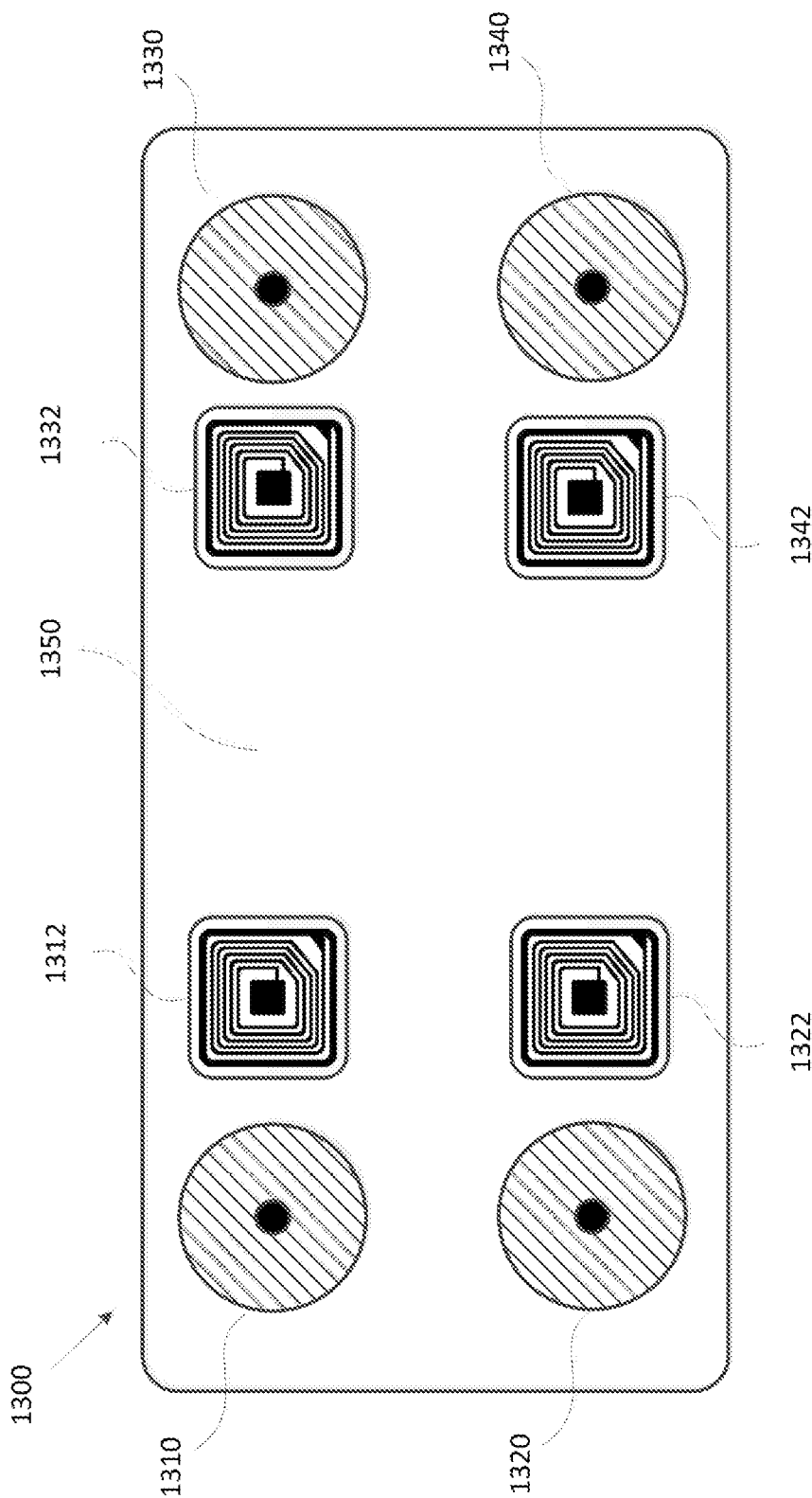
FIG. 13 shows a further example of the trackable electrode device.

Further, in some other embodiments, the trackable electrode device 100 may include a plurality of RF tags 120 (an example of which is shown in FIG. 13), each storing tag identification data associated with one or a group of electrode members 110.

As described hereinbefore, the substrate may be removably attached to the medical electrode(s) and the RF tag(s). For example, the substrate may include:
  a) a first substrate layer removably attached to one side of the medical electrode(s) and one side of the RF tag(s); and
  b) a second substrate layer removably attached to an opposite side of the medical electrode(s) and opposite side of the RF tag(s).

Accordingly, the electrode(s) and the RF tag may become separate from each other once the substrate or the substrate layers are removed. In some embodiments, the RF tag 120 and the electrode member 110 are attached to each other in a way that they overlap with each other. This may allow minimising the footprint of the trackable electrode device 100 on the patient's skin, and/or improving proximity to a RF reader when the RF reader is integrated with the cable for connecting the electrode member 110 with the medical device.

FIGS. 6(A) to 6(D) illustrate some other examples of the trackable electrode device 100 with the integral form of the substrate 130. In these examples, the RF tag 120 is integrated with the electrode member 110, and the substrate 130 is formed by at least a portion of the flexible sheet 210. For example, FIG. 6(A) and FIG. 6(B) show examples of the trackable electrode device 100. In these examples, the RF tag 120 is attached upon the electrode member 110, with the antenna 310 positioned around the electrode connecter 240 of the electrode member 110.

Further, FIG. 6(C) and FIG. 6(D) show some further examples of the trackable electrode device 100, in which the RF tag 120 is attached upon the electrode member 110 and positioned next to the electrode connecter 240 of the electrode member 110. Alternatively, the RF tag 120 may be attached in proximity to the electrode member 110 in any other suitable manner.

FIG. 7 shows an example of a system 10 for controlling the use of the trackable electrode device 100 in the medical device 200. The medical device 200 may be an electronic device for monitoring and/or recording the electrical signals received from the trackable electrode device 100, e.g., an electroencephalography (EEG) device, an electrocardiography (ECG) device, or the OLI™ mentioned hereinbefore.

Alternatively, the medical device 200 may be an electronic device for generating electrical signals to be fed to the trackable electrode device 100 for stimulating the patient, e.g., an electroconvulsive therapy (ECT) device, a defibrillator, or a transcutaneous electrical nerve stimulation (TENS) device. In another alternative embodiment, the medical device 200 may be any other suitable type of medical device that utilises electrodes in operation.

As shown in FIG. 7, in some embodiments, the medical device 200 includes an RF reader 270. The RF reader 270 of the system 10 is configured to read the RF tag 120 of the trackable electrode device 100. The RF reader 270 may be any suitable type of RF device that can read the RF tag 120. For example, if the RF tag 120 is an NFC tag, then the RF reader 270 may be an NFC reader. Alternatively, if the RF tag 120 is an RFID tag, then the RF reader 270 may be an RFID reader. Alternatively, the RF tag 120 may be any other suitable type of RF tag, and the RF reader 270 may be a device for reading that RF tag.

The RF reader 270 is electrically connected to the medical device 200 to receive any necessary electrical power from the medical device 200. The RF reader 270 is electronically connected to the medical device 200 to transmit signals to the medical device 200, including data representing the RF tag 120.

In embodiments, the RF reader 270 is attached to or integrated within the medical device 200, i.e., to a housing of the medical device 200 and/or to a printed circuit board (PCB) of the medical device 200, and the electrical and electronic connections between the RF reader 270 and the medical device 200 are direct connections, i.e., without separate cables. The RF reader 270 may be attached to an outside of the housing of the medical device 200, e.g., retrofitted to an pre-existing medical device; or integrated in and within the housing of the medical device 200 (i.e., regarded as an integrated part of the medical device 200 itself). When integrated in and within the housing of the medical device 200, the RF reader 270 may be assembled with other components of the medical device 200 during an assembly or manufacturing process, and/or assembled with electronic components on the PCB of the medical device 200. Further, the housing may be a sealed housing, including a water-resistant or water-proof sealed housing, and the RF reader 270 can be inside or outside the sealed housing, depending on the embodiment.

The medical device 200 includes an electrical signal interface 250 that transmits the electrical signals that are generated by or received by the medical device 200. The electrode member 110 of the trackable electrode device 100 is electrically connected to the medical device 200 via the electrical signal interface 250. The system 10 includes a conductive connector on the device that is referred to herein as a device-side connector 262. The device-side conductive connector 262 connects to the electrode-side conductive connector 240, so is of a cooperating connector type. The device-side connector 262 connects electrically to the electrode-side connector 240 to transmit the electrical signals between the medical device 200 and the electrode member 110. The device-side connector 262 and the cooperating electrode-side connector 240 are made of a conductive material (e.g., metal), can be cooperating fasteners, and in some embodiments have a shape similar to a female/male snap fastener, or have the form of a tab, wire or custom connector (as mentioned hereinbefore), including press-stud fasteners, e.g., where the electrode-side connector 240 is a male part (as shown in FIG. 2) and the device-side connector 262 is a cooperating female part.

Figure 7A:
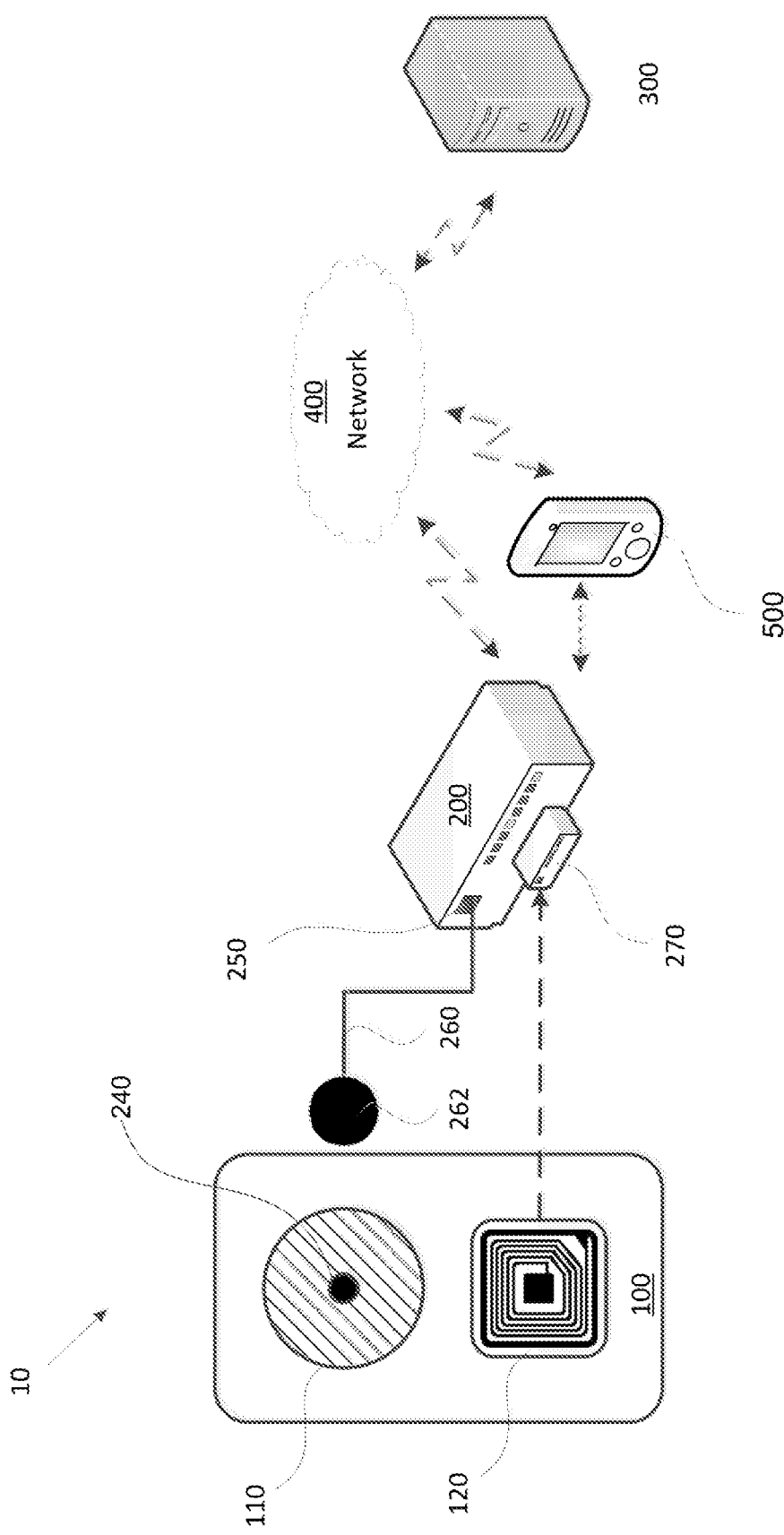
FIG. 7(A) shows an example of a system for controlling and/or monitoring the use of the trackable electrode device.

As shown in FIG. 7(A), in some embodiments, the system 10 includes a conductive cable 260 between the electrical signal interface 250 and the device-side connector 262. In an embodiment, the device-side connector 262 can be integrated into the end of the cable 260.

In some embodiments, the RF reader 270 may be integrated with the conductive cable 260. The conductive cable 260 includes the device-side connector 262 at the one end for connecting to the electrode member 110, and the RF reader 270 at or near the same end for reading the RF tag 120 attached to the electrode member 110. The other end of the conductive cable is configured for connection to the medical device 200, e.g., using a pre-existing plug. As the RF reader 270 and the device-side connector 262 are provided in proximity to each other in these embodiments, reading with the RF reader 270 and connecting the device-side connector 262 to the electrode member 110 can be performed by a single connection action. In addition, having the RF reader 270 next to the device-side connector 262 mitigates interference from other RF tags attached to other electrode members that may be nearby, and thus provides better signal quality and more accurate results. In an embodiment, the conductive cable 260 may include additional components, e.g., a memory for storing data.

Figure 7B:
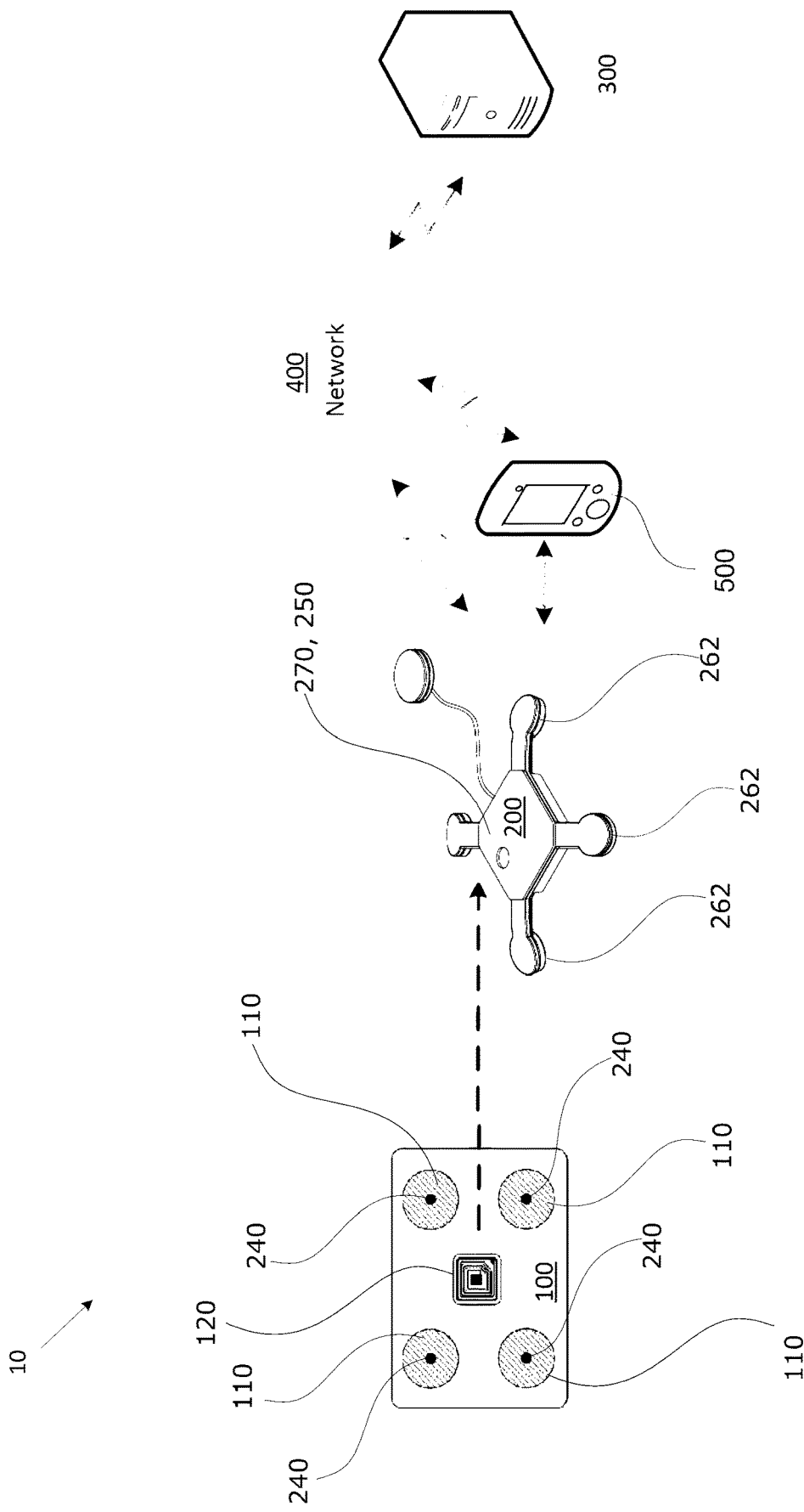
FIG. 7(B) shows an example of a system for controlling and/or monitoring the use of the trackable electrode device.

Referring to FIG. 7(B), there is provided an alternate embodiment where the system 10 does not include the conductive cable 260. Instead, the device-side connector 262 is mounted on or in the medical device 200, and may be regarded as an integrated part of the medical device 200 itself. In this embodiment, the device-side connector 262 may be referred to as an integrated device-side conductive connector. The device-side connector 262 may be inflexibly or flexibly mounted in or on at least part of the housing and/or an electronic circuit board (e.g., PCB) of the medical device 200 (e.g., as in the OLI™ device), without an intervening cable.

As described hereinbefore, the RF reader 270 and electrical signal interface 250 may also be integrated within the housing of the medical device 200 for reading the RF tag 120 of the trackable electrode device 100 that connects to the integrated device-side conductive connector 262. Further, the RF reader 270 may be arranged in close proximity to the device-side connector 262 on or in the medical device 200 for improved signal reception from the RF tag 120. The trackable electrode device 100 may include a plurality of electrode members 110 on the same substrate 130. For example, as shown in FIG. 7(B), the system 10 includes a trackable electrode device 100 that includes four electrode members 110 and a single RF tag 120 provided to a single substrate. The four electrode members 110 are arranged on the substrate to align and connect with the device-side connectors 262 provided to the housing of the medical device 200.

The medical device 200 may be in data communication with a server 300, via a communication network 400. The server 300 may take any suitable form, e.g., a cloud server, or a dedicated server. The server 300 may be a local server in a hospital, or a cloud-based server accessed by secure Internet connections.

The medical device 200 may also be in data communication with a terminal computing device 500 via the communication network 400 or via another method of wireless communication, such as but not limited to Bluetooth Low Energy technology. The terminal computing device 500 may be arranged to receive, store and/or display information relating to the data or information stored on the RF tag 120 and/or the signals received by or from the electrode member 110. The terminal computing device 500 may include computers, laptop, tablet, mobile device or any similar device. Moreover, the medical device 200 may be in communication with any number of terminal computing devices 500 or servers 300 at any given time.

The communications network 400 may take any appropriate form, e.g., the Internet and/or one or a number of local area networks (LANs). In practice, the medical device 200 and the server 300 may communicate via any appropriate mechanism, such as via wired and/or wireless connections, including, but not limited to mobile networks, private networks, such as an 802.11 network, the Internet, LANs, WANs, as well as via direct or point-to-point connections, such as Wi-Fi or Bluetooth.

Figure 8:
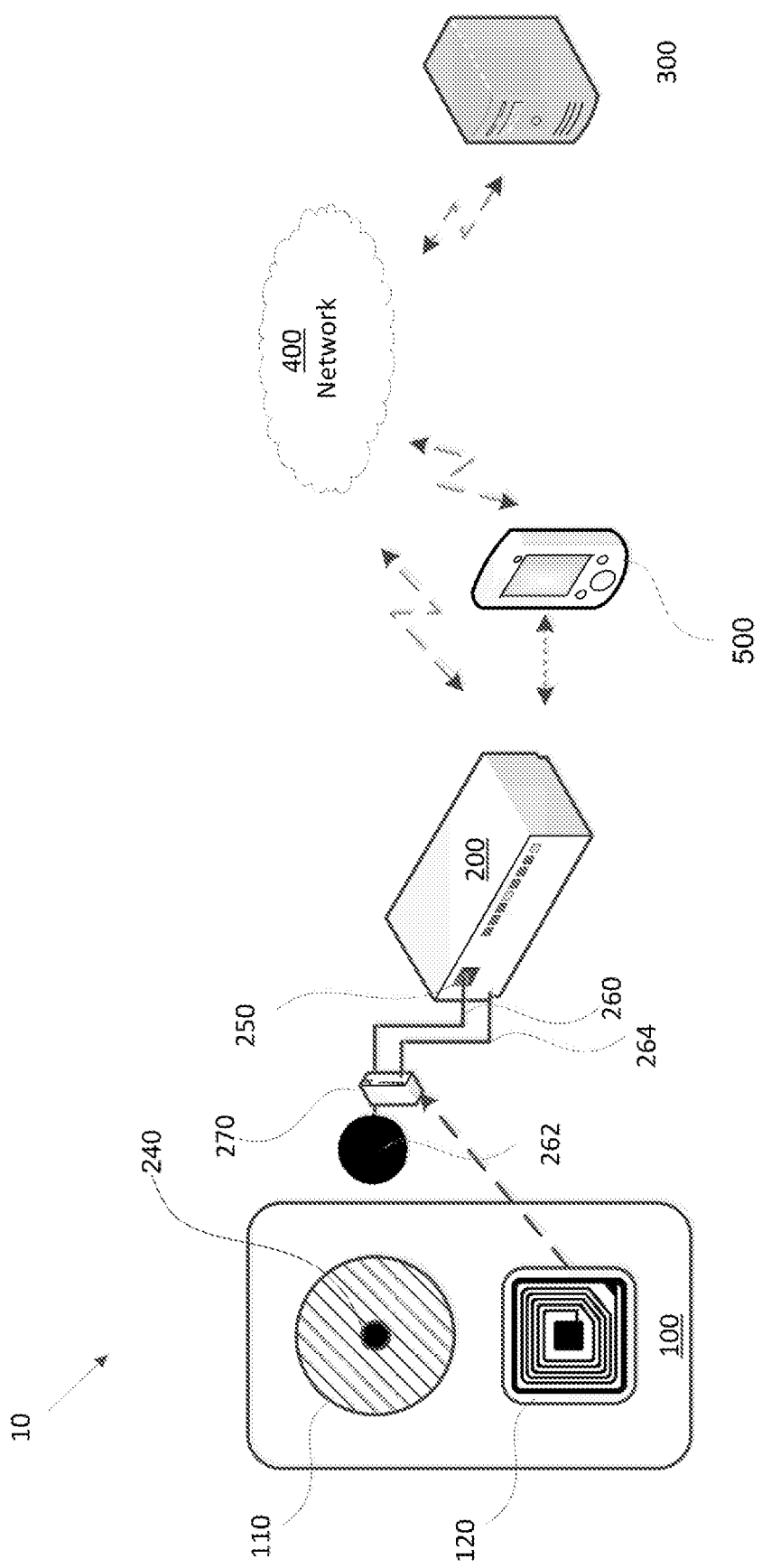
FIG. 8 shows another example of the system for controlling and/or monitoring the use of the trackable electrode device.

FIG. 8 illustrates an example in which the RF reader 270 is integrated with the conductive cable 260. As shown in FIG. 8, a power line 264 is used for supplying power to the RF reader 270 from the medical device 200, and/or for carrying signals between the RF reader 270 and the medical device 200. The conductive cable 260 further includes a signal line for carrying signals between the electrode-side connector 240 and the medical device 200.

Figure 9:
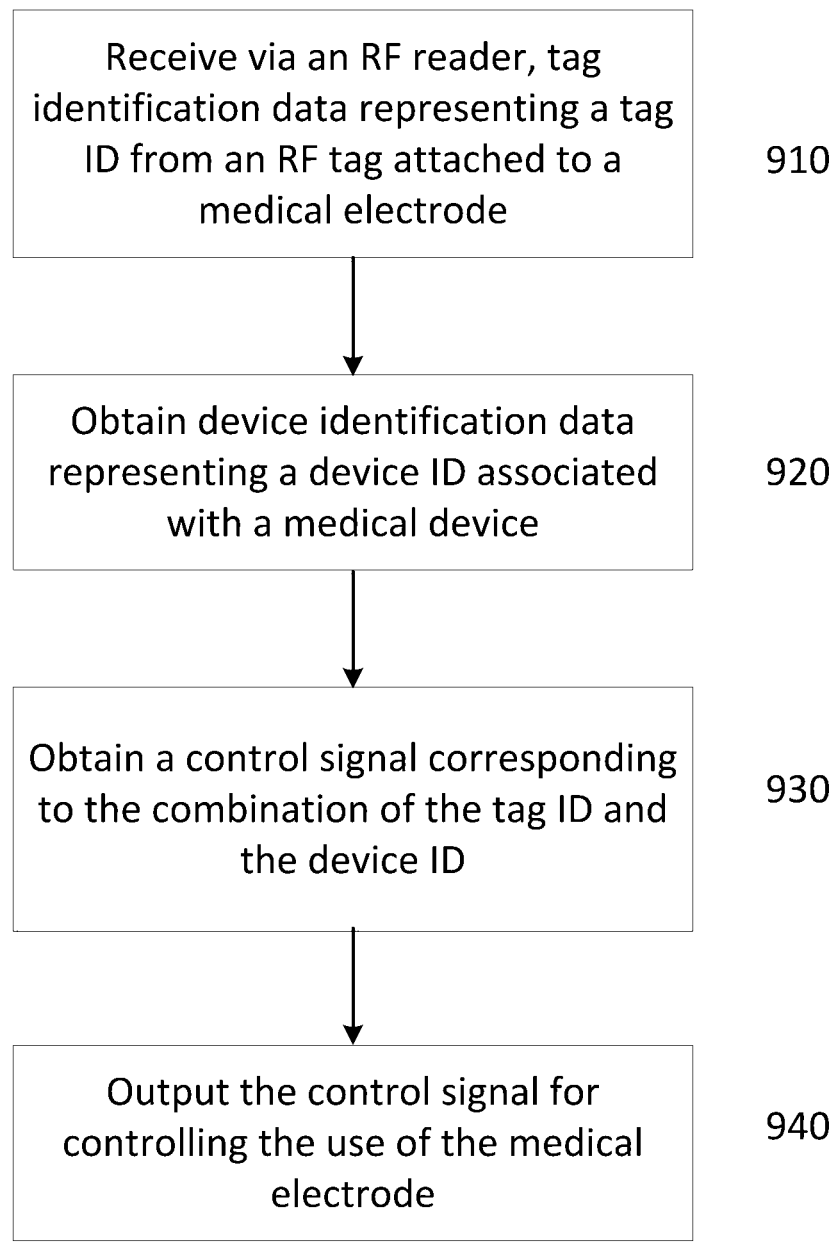
FIG. 9 illustrates an example workflow for controlling and/or monitoring the use of the trackable electrode device.

FIG. 9 illustrates an exemplary workflow executed by the medical device 200 shown in FIG. 7 or FIG. 8 for controlling the use of the trackable electrode device 100. Prior to or after the electrode member 110 of the trackable electrode device 100 is connected to the electrical signal interface 250 of the medical device 200, the medical device 200 uses the RF reader 270 to receive, from the RF tag 120 of the trackable electrode device 100, tag identification data representing a tag ID (Step 910). The tag ID is associated with the electrode member 110.

The medical device 200 then obtains device identification data, which represents a device identifier (ID) associated with the medical device 200 (Step 920). The device identification data may be stored in a memory of the medical device 200, or in a memory of one or more conductive cables configured for use with the medical device 200. Storing the device ID in the conductive cable can be useful when the conductive cable includes the RF reader 270.

Based on the received tag ID and the obtained device ID, at Step 930 the medical device 200 obtains a control signal corresponding to the combination of the tag ID and the device ID, e.g., by querying the server 300. The medical device 200 may send both the tag ID and the device ID to the server 300 via the communication network 400. Based on the combination of the tag ID and the device ID, the server 300 determines a control signal indicating the compatibility between the medical device 200 and the trackable electrode device 100, and sends the control signal back to the medical device 200. The server 300 determines the compatibility control signal by using data representing the compatibilities between the devices ID and the tag IDs, e.g., in compatibility tables.

Alternatively, in some embodiments, the medical device 200 may be offline, i.e., the medical device 200 may be not connected to the server 300. In those cases, the medical device 200 may be configured to determine the control signal based on a predefined algorithm, e.g., by executing a computer program pre-stored on the medical device 200, and based on pre-stored data in the medical device 200. The pre-stored data represent the compatibilities between the devices ID and the tag IDs, e.g., as compatibility tables. The offline medical device 200 has the tag ID pre-stored, and this can be updated sporadically, e.g., in a software update. Therefore, based on the combination of the tag ID and the device ID, the medical device 200 determines the compatibility between the devices ID and the tag IDs, e.g., in compatibility tables.

Upon receiving the control signal from the server 300 or determining the control signal by executing the computer program pre-stored on the medical device 200 and accessing the pre-stored data, the medical device 200 then controls the use of the trackable electrode device 100 according to the control signal (Step 940), e.g., by allowing the use of a compatible trackable electrode device 100, or prohibiting the use of an incompatible trackable electrode device 100.

Alternatively, in some embodiments, the medical device 200 may not be directly connected to the communication network 400. Instead, the medical device 200 is communicatively connected to a terminal computing device 500, the latter being connected to the communication network 400 and capable of communicating with the server 300. The terminal computing device 500 may be any suitable terminal computing device, e.g., a smart phone, a tablet computer, a laptop computer, a desktop computer, a personal digital assistant, or a smart wearable device.

The data communication between the medical device 200 and the terminal computing device 500 may take any suitable form, for example, through wired and/or wireless connection. In some embodiments, the medical device 200 and the terminal computing device 500 may be connected to each other via Wi-Fi, NFC, or Bluetooth connections. Accordingly, to control the use of the trackable electrode device 100, the medical device 200 uses the RF reader 270 to receive, from the RF tag 120 of the trackable electrode device 100, tag identification data representing a tag ID. The tag ID is associated with the electrode member 110.

The medical device 200 then obtains device identification data, which represents a device ID associated with the medical device 200. The device identification data may be stored in a memory of the medical device 200. The medical device 200 then sends the tag ID and the device ID to the terminal computing device 500. The terminal computing device 500 determines the control signal corresponding to the combination of the tag ID and the device ID by querying the server 300. The server 300 determines the compatibility between the medical device 200 and the electrode member 110 based on the combination of the tag ID and the device ID, and sends data indicating the compatibility back to the terminal computing device 500. Based on the data received from the server 300, the terminal computing device 500 determines a control signal and sends the control signal to the medical device 200. Alternatively, in some embodiments, the medical device 200 may be not be connected to the server 300 or the terminal computing device 500. In those cases, the medical device 200 may be configured to determine the control signal based on a predefined algorithm, e.g., by executing a computer program pre-stored on the medical device 200.

Upon receiving the control signal from the terminal computing device 500, or upon determining the control signal by executing the computer program pre-stored on the medical device 200, the medical device 200 then controls the use of the electrode member 110 according to the control signal.

Figure 10:
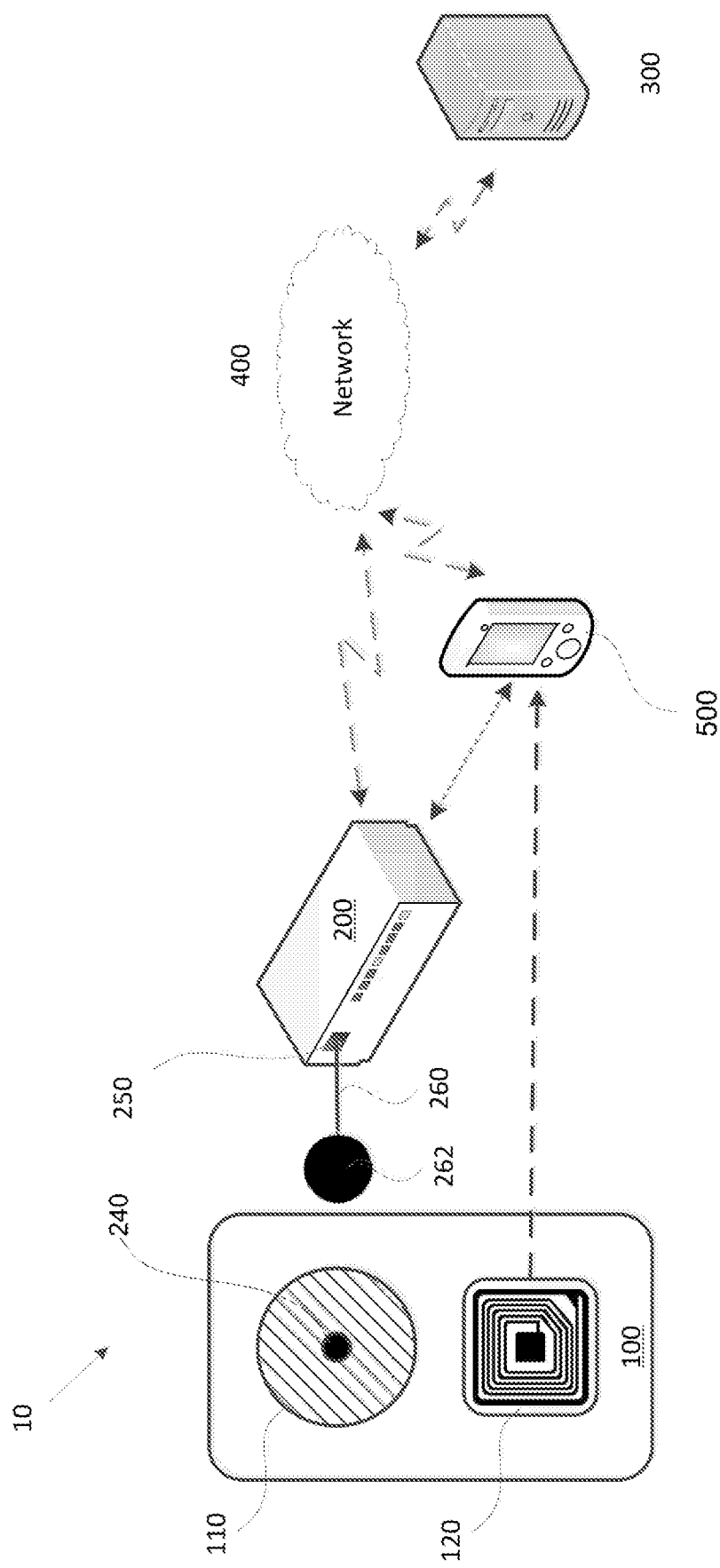
FIG. 10 shows a further example of the system for controlling and/or monitoring the use of the trackable electrode device.

FIG. 10 shows a further example of the system 10 for controlling the use of the trackable electrode device 100 in the medical device 200. In this example, the medical device 200 does not include the RF reader 270. The terminal computing device 500, instead, includes an RF reader (e.g., an NFC reader, or an RFID reader) that can read the RF tag 120.

Accordingly, to control the use of the trackable electrode device 100, the terminal computing device 500 uses its RF reader to receive, from the RF tag 120, tag identification data representing a tag ID associated with the electrode member 110. The terminal computing device 500 then obtains device identification data, which represents a device ID associated with the medical device 200. The device identification data may be acquired by the terminal computing device 500 from the medical device 200 via data communication. Alternatively, the device identification data may be obtained by the terminal computing device 500 in any other suitable manner, for example, by a user inputting the device ID of the medical device 200 into the terminal computing device 500, or by the terminal computing device 500 scanning a barcode, a quick response (QR) code, or any other type of machine readable code attached to the medical device 200.

The terminal computing device 500 then obtains the control signal corresponding to the combination of the tag ID and the device ID, e.g., by querying the server 300. The server 300 determines the compatibility between the medical device 200 and the electrode member 110 based on the combination of the tag ID and the device ID, and sends data indicating the compatibility to the terminal computing device 500. Based on the data received from the server 300, the terminal computing device 500 determines and outputs a control signal.

For example, the terminal computing device 500 may send the control signal to the medical device 200, to instruct the medical device 200 to use or not use the electrode member 110 according to the control signal. Alternatively, the terminal computing device 500 may output the control signal in any other suitable manner. For example, the terminal computing device 500 may display a control message on a screen of the terminal computing device 500 to inform a user of the medial device 200, the control message indicating whether and/or how the electrode member 110 should be used with the medical device 200. Alternatively or additionally, the terminal computing device 500 may trigger an alarm if it determines that the electrode member 110 is incompatible with the medical device 200.

In some embodiments, a manufacturer of the trackable electrode device 100 (or the electrode member 110) or a relevant regulatory authority may set a shelf life or expire date for the electrode member 110. The server 300 may determine the shelf life or expire date of the electrode member 110 based on the tag ID, and send it to the medical device 200, e.g., as part of the control signal, to control the use of the trackable electrode device 100 accordingly. For example, if the shelf life of the electrode member 110 has expired, the medical device 200 may notify the user and require a replacement of the trackable electrode device 100.

In some embodiments, a manufacturer of the trackable electrode device 100 (or the electrode member 110) or a relevant regulatory authority may set a maximum attachment duration or an ideal attachment duration that the electrode member 110 can be attached to the body of a patient. The server 300 may determine the maximum attachment duration of the electrode member 110 based on the tag ID, and send it to the medical device 200, e.g., as part of the control signal, to control the use of the trackable electrode device 100. For example, if the electrode member 110 has been used for a period of time exceeding the maximum attachment duration, the medical device 200 may notify the user and require a replacement of the trackable electrode device 100.

In some embodiments, the medical device 200 monitors the use of the trackable electrode device 100, and reports the usage to the server 300. This may include the medical device 200 reporting to the server 300 any abnormality occurred during the use of the trackable electrode device 100. For example, a manufacturer of the trackable electrode device 100 or a relevant regulatory authority may set a recommended attachment duration that the electrode member 110 can be attached to the body of a patient. The recommended attachment duration may be determined by the server 300 based on the tag ID, and sent to the medical device 200, e.g., as part of the control signal. If during the use of the trackable electrode device 100, the connection between the electrode member 110 and the patient's body is lost or unstable after a period of time less than the recommended attachment duration, the medical device 200 may report this failure to the server 300. This allows the server 300 to collect usage data from multiple medical devices that use the trackable electrode devices, and to provide useful information to manufacturers and/or future users of the medical devices and the trackable electrode devices. For example, the recommended attachment duration and/or the maximum attachment duration may be updated by the server 300 based on the collected usage data, which allows determination of a more accurate recommended attachment duration and/or maximum attachment duration, and thus optimises the use of the trackable electrode device 100.

As another example, the medical device 200 may further monitor the signal performance of the electrical signals received from the trackable electrode device 100. The medical device 200 may include a data storage device that stores data representing the tag ID associated with the trackable electrode device 100 linked to the device ID associated with the medical device 200, e.g., in a database. Further, the medical device 200 may store the tag ID and the device ID linked to signals recorded by the medical device 200 using the trackable electrode device 100 in the data storage device, e.g., in a database.

For example, an acceptable signal-to-noise ratio (SNR) may be predefined by a manufacturer of the medical device 200 or a regulatory institution, and obtained by the medical device 200. If the medical device 200 detects that the SNR of the electrical signals received from the trackable electrode device 100 have fallen lower than the acceptable signal-to-noise ratio, the medical device 200 may trigger an alarm to notify the user and allow the user to manual check the attachment of the electrode member 110 to the patient and the connection between the electrode member 110 and the medical device 200. The medical device 200 may report the result to the server 300. This information may be collected by the server 300 and used for providing feedback to the manufacturer of the trackable electrode device 100 or the electrode member 110. For example, the manufacturer may use this information to improve product training for users, or to determine whether the trackable electrode device 100 has quality issues and should be recalled.

The trackable electrode devices 100 with quality issues may be recorded by or registered at the server 300, so that future use of these devices may be prohibited or warned. If the server 300 detects that a tag ID is associated with a trackable electrode device 100 that has quality issues or should be recalled, the server 300 may send this information to the medical device 200, which can then notify the user regarding the product recall and/or prohibit the use of the trackable electrode device 100, e.g., by displaying a notification on a user interface and/or control the medical device 200 to stop or pause operating. This may provide a more effective and efficient way of quality control, and a more thorough and timely way of addressing product recalls or potential defects of medical electrode products, even when the products have been sold via different distributors. This also allows the user of the electrodes (e.g., medical staff) to be informed of the potential defects of the trackable electrode device 100, and assist the user to optimise the use of the trackable electrode device 100 and avoid potentially unreliable use.

Figure 11:
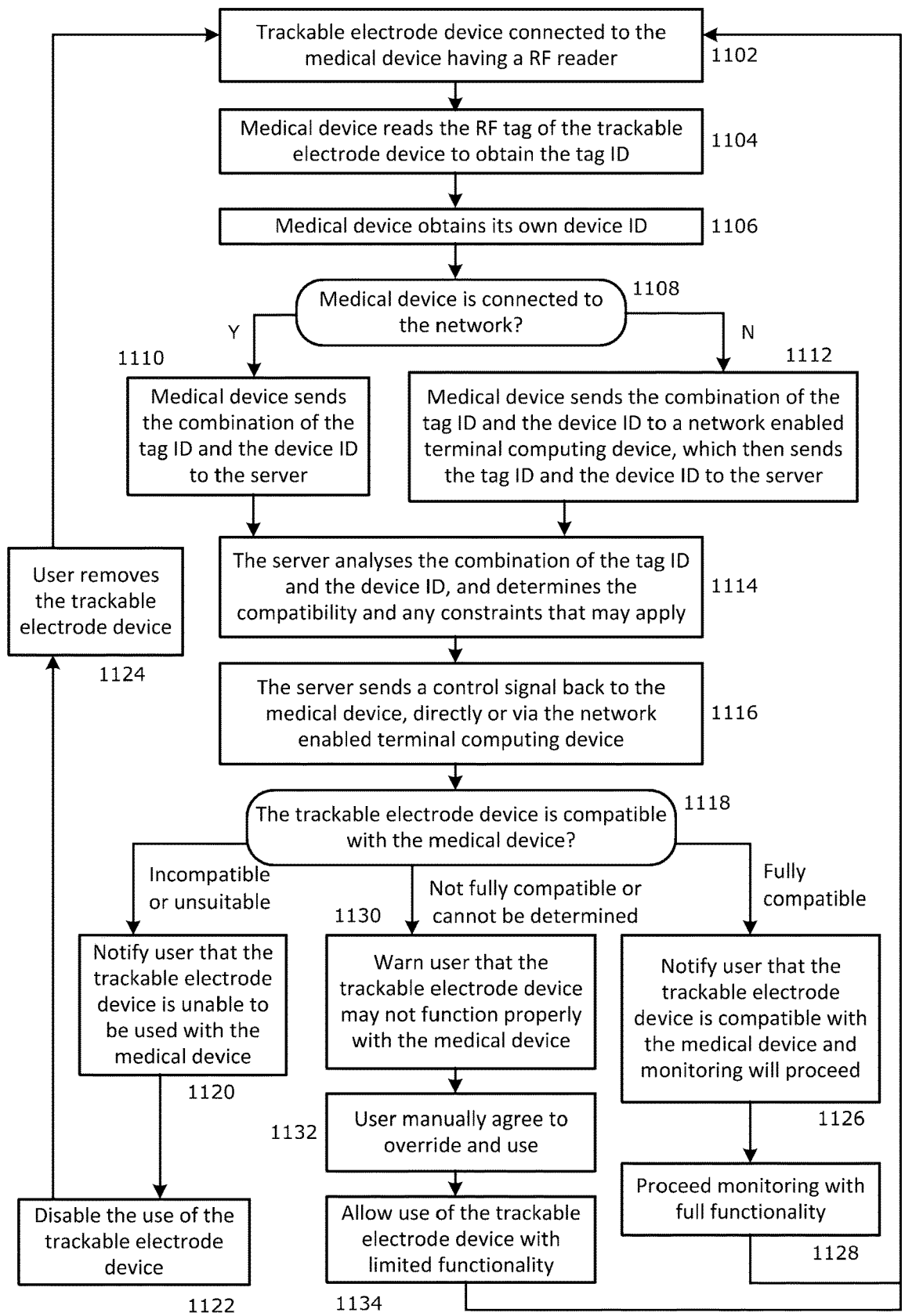
FIG. 11 illustrates a detailed example of the workflow for controlling and/or monitoring the use of a trackable electrode device.
Figure 12:
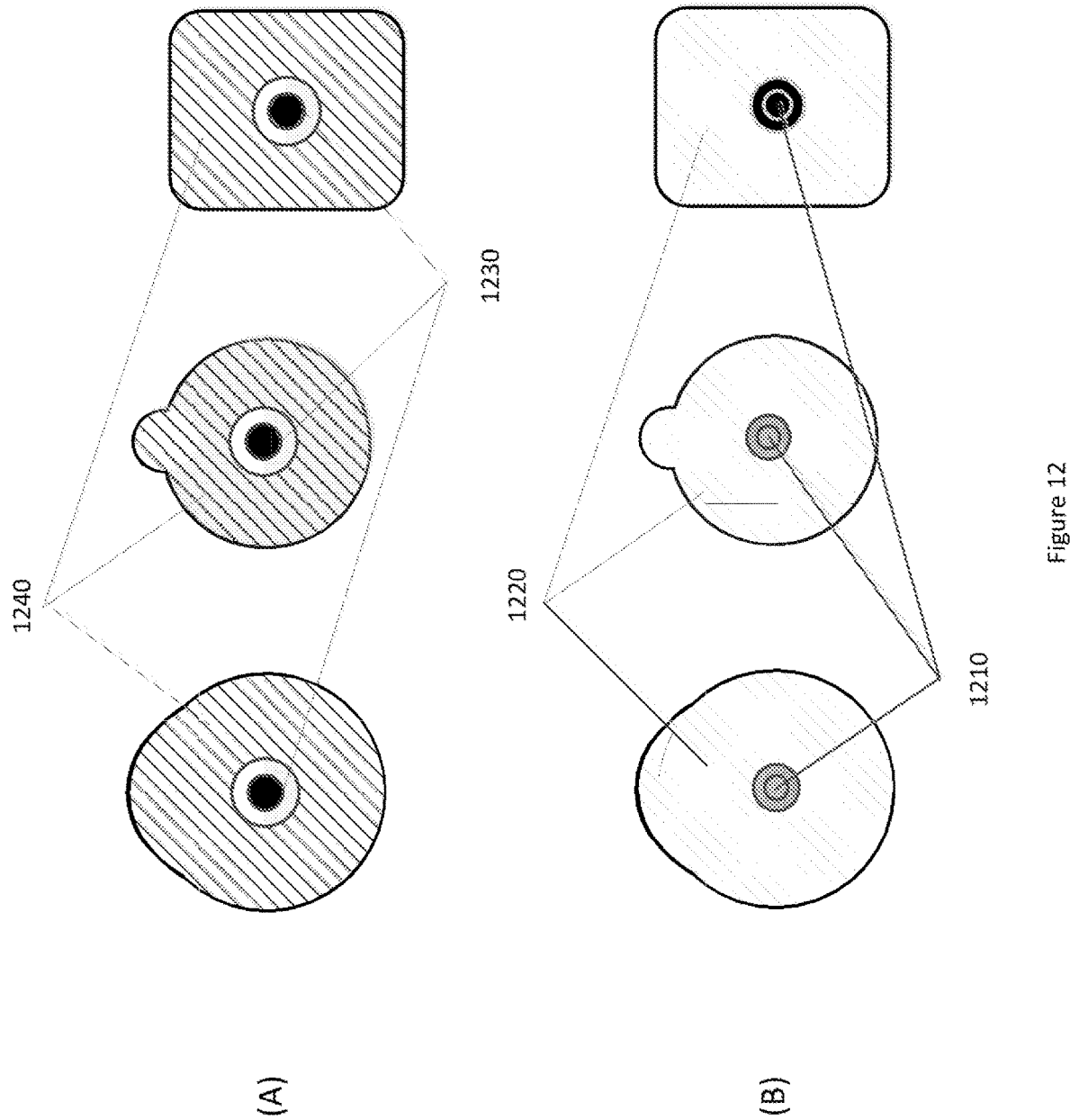
FIGS. 12A and 12B show front side and back side views of different types of medical electrodes, respectively.

FIG. 11 illustrates an exemplary workflow executed by the medical device 200 shown in FIG. 7, 8 or 10 for controlling the use of the trackable electrode device 100. In this example, the medical device 200 is a monitoring device, e.g., an electroencephalography (EEG) device, or an electrocardiography (ECG) device.

Firstly, at Step 1102, the trackable electrode device 100 is electrically connected to the medical device 200, e.g., by connecting the electrode member 110 to the electrical signal interface 250 of the medical device 200. At Step 1104, the medical device 200 uses the RF reader 270 to receive, from the RF tag 120 of the trackable electrode device 100, tag identification data representing a tag ID associated with the electrode member 110.

At Step 1106, the medical device 200 obtains device identification data, which represents a device identifier (ID) associated with the medical device 200, e.g., by retrieving the device ID from a memory of the medical device 200. At Step 1108, the medical device 200 determines whether it is connected to the communication network 400. If the medical device 200 is connected to the communication network 400, the medical device 200 sends the combination of the tag ID and the device ID to the server 300 at Step 1110. Preferably, the server 300 is a cloud server. In some embodiments, the server 300 may alternatively be a dedicated server.

Alternatively, if the medical device 200 is not connected to the communication network 400, the medical device 200 sends the combination of the tag ID and the device ID to the network enabled terminal computing device 500, which then sends the tag ID and the device ID to the server 300 (Step 1112).

At Step 1114, the server 300 analyses the combination of the tag ID and the device ID, and determines the compatibility between the medical device 200 and the electrode member 110. The server 300 may further determine whether any constraints may apply in using the trackable electrode device 100 with the medical device 200. For example, the server 300 may determine whether the trackable electrode device 100 has expired (e.g., the trackable electrode device 100 has passed its shelf life, or the trackable electrode device 100 is a defective product and needs to be recalled.) Based on the analysis, the server 300 sends a control signal back to the medical device 200 at Step 1116. The control signal may be sent directly to the medical device 200 if the medical device 200 is network enabled. Alternatively, the control signal may be sent to the medical device 200 via the network enabled terminal computing device 500.

The medical device 200 then determines whether the trackable electrode device 100 is suitable for using with the medical device 200 (Step 1118). For example, if the control signal received from the server 300 indicates that the trackable electrode device 100 is incompatible or unsuitable to be used with the medical device 200, the medical device 200 may determine that the trackable electrode device 100 should not be used.

In some embodiments, if the trackable electrode device 100 has expired (e.g., the shelf life of the trackable electrode device 100 has passed), or if the trackable electrode device 100 is a defective product, the medical device 200 or the server 300 may also determine that the trackable electrode device 100 is unsuitable to be used.

In some embodiments, if the electrical signals received from the trackable electrode device 100 via the electrical signal interface 250 are illegible signals (e.g., the signal strength exceeds or falls below a predetermined threshold), the medical device 200 or the server 300 may also determine that the trackable electrode device 100 should not be used.

Once determined that the trackable electrode device 100 is unsuitable to be used, the medical device 200 may be configured to prohibit the use of the trackable electrode device 100. The medical device 200 may notifying the user that the trackable electrode device 100 is unable to be used with the medical device 200 (Step 1120).

The medical device 200 may further disable the signal communication via the electrical signal interface 250 (Step 1122), until the user disconnects the electrode member 110 of the trackable electrode device 100 from the medical device 200 (Step 1124). If another trackable electrode device 100 is subsequently connected to the medical device 200, the medical device 200 loops back to Step 1102 and restarts the process.

Alternatively, if at Step 1118 the medical device 200 determines that the trackable electrode device 100 is suitable for using with the medical device 200, e.g., based on a control signal indicating the compatibility between the trackable electrode device 100 and the medical device 200, the medical device may notify the user that the trackable electrode device 100 is compatible with the medical device 200 and that the monitoring will proceed (Step 1126). The medical device 200 then proceeds to Step 1128 to allow the use of the trackable electrode device 100 with full functionality.

Alternatively, if at Step 1118 the medical device 200 determines that the trackable electrode device 100 and the medical device 200 are not fully compatible, or the combination of the tag ID and the device ID does not provide sufficient information to determine whether the trackable electrode device 100 and the medical device 200 are compatible (e.g., if the control signal indicates that the combination of the tag ID and the device ID is unrecognisable), the medical device 200 may warn the user that the trackable electrode device 100 cannot be guaranteed to function properly with the medical device 200 (Step 1130), and require user input to confirm whether the user agrees to use the trackable electrode device 100 (Step 1132).

Upon receiving the user input that authorises the use of the trackable electrode device 100, the medical device 200 proceeds to Step 1134 to monitor the electrical signals by using the trackable electrode device 100. Preferably, only a limited number of functions of the medical device 200 are allowed to be used. The functions to be used may be determined by the medical device 200 based on the control signal received from the server 300. Alternatively, to track the application of the trackable electrode device 100, the electrical signals are recoded by the medical device 200, and/or transmitted to the enabled terminal computing device 500 or the server 300, to monitor the performance of the medical electrodes in the trackable electrode device 100.

As described hereinbefore, in some embodiments, the medical device 200 may be not connected to the server 300 or the terminal computing device 500. In those cases, the medical device 200 may be configured to determine itself the control signal based on a predefined algorithm, e.g., by executing a computer program pre-stored on the medical device 200. The pre-stored computer program determines the compatibility between the medical device 200 and the trackable electrode device 100 based on the combination of the device ID and the tag ID. Upon determining the control signal by executing the pre-stored computer program, the medical device 200 then controls the use of the electrode member 110 according to the control signal.

The methods and systems described in this disclosure provide an effective and efficient way of identifying whether the electrodes to be used are in fact suitable for being used with the medical device.

According to some embodiments, the methods and systems may also be used as a tool for manufacturers of electrodes or medical devices to track the application of the medical electrodes, and to monitor the performance of the medical electrodes. This may reveal elements of the electrode that could impact its performance, and may provide valuable information for product improvement or trainings for users.

According to some embodiments, the methods and systems may also be used to prevent or reduce overuse of electrodes, for example, by prohibiting an electrode to be used for longer than its intended shelf life or usable duration. This may ensure that the electrode when being used can provide desirable signal quality, and the monitoring or treatment results from using the electrodes are accurate.

Further, as shown in FIG. 13, also described herein is a trackable electrode device 1300, including:
a) a plurality of medical electrodes (1310, 1320, 1330, 1340);
b) a corresponding plurality of radio-frequency (RF) tags (1312, 1322, 1332, 1342), each having an identifier (ID) that identifies a corresponding one of the plurality of medical electrodes; and
c) at least one substrate 1350 attached to the plurality of medical electrodes and the plurality of RF tags. The substrate 1350 may be a form of the removable substrate 130 or of the integrated substrate 130.

Further, the term "patient" used hereinbefore includes both human and animal patients and users. Accordingly, the medical device 200 may include medical devices, well-being equipment and sport-monitoring equipment, for humans or veterinary devices for animals.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Many modifications will be apparent to those skilled in the art without departing from the scope of the present invention.

Throughout this specification and the claims which follow, unless the context requires otherwise, the word "comprise", and variations such as "comprised", "comprises" or "comprising", will be understood to imply the inclusion of a stated integer or step or group of integers or steps but not the exclusion of any other integer or step or group of integers or steps.

As used herein, a, an, the, at least one, and one or more are used interchangeably, and refer to one or to more than one (i.e. at least one) of the grammatical object. By way of example, "an element" means one element, at least one element, or one or more elements.

The invention claimed is:

1. A system including:
at least one medical electrode;
a radio-frequency (RF) tag with an identifier (ID) that identifies the at least one medical electrode; and
at least one substrate that attaches the at least one medical electrode to the RF tags;
a medical device having a device identifier (ID) that identifies the medical device; and
a radio-frequency (RF) reader that operates with the medical device, the RF tag being readable by the RF reader,
wherein use of the medical electrode with the medical device is controlled based on a control signal determined from a combination of the ID and the device ID.

2. The system of claim 1, wherein the at least one substrate is a removable substrate that is arranged to be manually removable from the medical electrode and the RF tag.

3. The system of claim 2, wherein the at least one substrate includes:
a first substrate layer removably attached to one side of the medical electrode and one side of the RF tag; and
a second substrate layer removably attached to an opposite side of the medical electrode and opposite side of the RF tag.

4. The system of claim 1, wherein the at least one substrate is an integral substrate that is arranged to maintain the at least one medical electrode together with the RF tag in use.

5. The system of claim 1, including a plurality of medical electrodes and a shared substrate that holds the plurality of medical electrodes and the RF tag together.

6. A system including:
a radio-frequency (RF) reader that reads an RF tag attached to a medical electrode to determine a tag identifier (ID) that identifies the medical electrode; and
a medical device including the RF reader that operates with the medical electrode having a device identifier (ID) that identifies the medical device,
wherein use of the medical electrode with the medical device is controlled based on a control signal determined from a combination of the tag ID and the device ID.

7. The system of claim 6, the medical device, a server or a terminal computing device including a data storage device that stores data representing the tag ID linked to the device ID.

8. The system of claim 7, wherein the data storage device stores data representing the tag ID and the device ID linked to signals recorded by the medical device using the medical electrode.

9. The system of claim 6, including a control system that:
receives the tag ID and the device ID;
accesses data representing pre-determined compatibilities between a plurality of stored device IDs and stored tag IDs stored in a data storage device;
generates the control signal by determining whether the tag ID and the device ID are compatible according to the pre-determined compatibilities; and
controls use of the medical electrode with the medical device based on the control signal determined from the combination of the tag ID and the device ID.

10. A method comprising the steps of:
reading an RF tag attached to a medical electrode to determine a tag identifier (ID) that identifies the medical electrode;
accessing a device identifier (ID) that identifies a medical device that operates with the medical electrode; and
controlling use of the medical electrode with the medical device based on a control signal determined from a combination of the tag ID and the device ID.

11. The method of claim 10, including storing data representing the tag ID linked to the device ID.

12. The method of claim 10, including storing data representing the tag ID and the device ID linked to signals recorded by the medical device using the medical electrode.

13. The method of claim 12, further including the steps of:
receiving the tag ID and the device ID;
accessing data representing pre-determined compatibilities between a plurality of stored device IDs and stored tag IDs stored in a data storage device; and
generating the control signal by determining whether the tag ID and the device ID are compatible according to the pre-determined compatibilities.

14. A computer-implemented method, including the steps of:
receiving, via a radio-frequency (RF) reader, tag identification data representing a tag identifier (ID) from an RF tag attached to a medical electrode;
accessing device identification data representing a device identifier (ID) associated with a medical device operable to use at least one medical electrode;
determining a control signal corresponding to the combination of the tag ID and the device ID; and
controlling the use of the medical electrode with the medical device based on the control signal.

15. The method of claim 14, wherein the control signal is determined by:
sending the combination of the tag ID and the device ID to an external device; and
receiving the control signal from the external device.

16. The method of claim 15, wherein controlling the use of the medical electrode with the medical device further includes:
outputting an alert if the use of the medical electrode is prohibited or limited.

17. A computer-implemented method, including the steps of:
receiving, from a medical device operable to use at least one medical electrode, tag identification data representing a tag identifier (ID), the tag identification data being obtained from an RF tag attached to the medical electrode;
obtaining device identification data representing a device identifier (ID) associated with the medical device;
determining a control signal corresponding to the combination of the tag ID and the device ID; and
outputting the control signal that controls the use of the medical electrode with the medical device.

18. The method of claim 17, wherein outputting the control signal includes sending the control signal to the medical device.

19. An assembly including:
a medical device that monitors or generates electrical signals and having a device identifier (ID) that identifies the medical device;
a conductive connector in or on the medical device for connecting to a medical electrode; and
a radio-frequency (RF) reader in or on the medical device for reading an RF tag attached to the medical electrode to determine a tag identifier (ID) that identifies the medical electrode,
wherein use of the medical electrode with the medical device is controlled based on a control signal determined from a combination of the tag ID and the device ID.

* * * * *